(12) United States Patent
Adam

(10) Patent No.: US 9,890,130 B2
(45) Date of Patent: Feb. 13, 2018

(54) PHENOLIC EPOXY COMPOUNDS

(71) Applicant: EMPIRE TECHNOLOGY DEVELOPMENT LLC, Wilmington, DE (US)

(72) Inventor: Georgius Abidal Adam, Edensor Park (AU)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/768,218

(22) PCT Filed: Nov. 21, 2013

(86) PCT No.: PCT/US2013/071204
§ 371 (c)(1),
(2) Date: Aug. 15, 2015

(87) PCT Pub. No.: WO2014/126626
PCT Pub. Date: Aug. 21, 2014

(65) Prior Publication Data
US 2016/0009672 A1    Jan. 14, 2016

Related U.S. Application Data

(60) Provisional application No. 61/765,324, filed on Feb. 15, 2013.

(51) Int. Cl.
| | |
|---|---|
| *C07D 301/28* | (2006.01) |
| *C07D 303/23* | (2006.01) |
| *C07D 303/27* | (2006.01) |
| *C07C 215/50* | (2006.01) |
| *C08G 59/08* | (2006.01) |
| *C07D 303/30* | (2006.01) |
| *C08G 59/32* | (2006.01) |
| *C07C 39/12* | (2006.01) |
| *C07C 43/178* | (2006.01) |
| *C07D 303/36* | (2006.01) |
| *C07C 37/20* | (2006.01) |
| *C07C 41/01* | (2006.01) |
| *C07C 213/02* | (2006.01) |

(52) U.S. Cl.
CPC .......... *C07D 303/30* (2013.01); *C07C 37/20* (2013.01); *C07C 39/12* (2013.01); *C07C 41/01* (2013.01); *C07C 43/1785* (2013.01); *C07C 213/02* (2013.01); *C07C 215/50* (2013.01); *C07D 301/28* (2013.01); *C07D 303/23* (2013.01); *C07D 303/27* (2013.01); *C07D 303/36* (2013.01); *C08G 59/08* (2013.01); *C08G 59/3218* (2013.01)

(58) Field of Classification Search
CPC .. C07D 301/28; C07D 303/23; C07D 303/27; C07C 215/50; C08G 59/08; C08G 59/3218
See application file for complete search history.

(56) References Cited

U.S. PATENT DOCUMENTS

| 773,510 A | 10/1904 | Lindsay et al. |
|---|---|---|
| 2,091,965 A | 9/1937 | Cherry |

(Continued)

FOREIGN PATENT DOCUMENTS

| CN | 1047311 A | 11/1990 |
|---|---|---|
| CN | 1207114 A | 2/1999 |

(Continued)

OTHER PUBLICATIONS

JP 2000147773 (PD May 26, 2000—machine translation).*
International Search Report for International Application No. PCT/US2013/071204 mailed on May 14, 2014.
Cech, Characteristics of Bis F and Phenol Novolac Epoxy Resins, Compositional differences and their effect on Performance, pp. 1-16.
Cheng et al., Synthesis and characterization of novel multifunctional epoxy resin, *Chinese Chemical Letters* (Apr. 2007), 18(4):469-472.
Huntsman, Huntsman to Further Expand Multifunctional Epoxy Resins Capacity and Capability, accessed at: http://www.huntsman.com/eng/News/News/Huntsman_to_Further_Expand_Multifunctional_Epoxy_Resins_Capacity_and_Capability/index.cfm?PageID=8583&News_ID=8060&style=72, pp. 1-2 pages (Sep. 14, 2011).

(Continued)

*Primary Examiner* — Valerie Rodriguez-Garcia
(74) *Attorney, Agent, or Firm* — Pepper Hamilton LLP

(57) ABSTRACT

Disclosed herein are compositions and methods of making phenolic compounds, and resins comprising these phenolic compounds. The compounds include multifunctional epoxies, amino glycidyl derivatives, and multi-functional amines prepared from hydroxymethyl derivatives of phenols and bisphenols. In one embodiment, a compound is of formula I

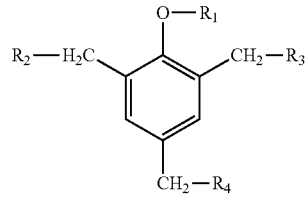

wherein $R_1$ is H or Z; each $R_2$, $R_3$, and $R_4$, independently, are —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —O—Z, —CH$_2$—O—Z, —CH$_2$CH$_2$—O—Z, —CH$_2$OH, —CH$_2$NH$_2$, —O—C—(CH$_3$)$_3$, or —O-(alkylene)-CH$_3$; and Z is

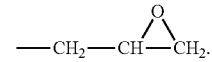

10 Claims, No Drawings

(56) References Cited

U.S. PATENT DOCUMENTS

| | | | |
|---|---|---|---|
| 2,220,834 A * | 11/1940 | Bruson | C07D 295/096 544/121 |
| 2,541,142 A | 2/1951 | Zief et al. | |
| 2,980,676 A | 4/1961 | Zuppinger et al. | |
| 3,425,964 A | 2/1969 | Stanley | |
| 3,546,156 A | 12/1970 | Baronnier et al. | |
| 3,726,835 A | 4/1973 | Bertozzi | |
| 3,741,799 A | 6/1973 | Kulhanek et al. | |
| 3,957,524 A | 5/1976 | Doughty et al. | |
| 4,003,873 A | 1/1977 | Smith | |
| 4,038,455 A | 7/1977 | Wampetich | |
| 4,256,844 A | 3/1981 | Martin et al. | |
| 4,301,083 A | 11/1981 | Yoshimura et al. | |
| 4,369,290 A | 1/1983 | Evans et al. | |
| 4,374,126 A | 2/1983 | Cardarelli et al. | |
| 4,623,701 A | 11/1986 | Massingill | |
| 4,661,568 A | 4/1987 | Koenig et al. | |
| 4,853,145 A | 8/1989 | Schmid et al. | |
| 4,883,826 A | 11/1989 | Marugg et al. | |
| 4,900,873 A | 2/1990 | Kakemoto et al. | |
| 5,028,458 A | 7/1991 | Mineck | |
| 5,354,798 A | 10/1994 | Tsukahara et al. | |
| 5,496,890 A | 3/1996 | Sackmann et al. | |
| 5,908,902 A | 6/1999 | Pfeil et al. | |
| 5,939,515 A | 8/1999 | Guenther et al. | |
| 5,965,671 A | 10/1999 | Ma et al. | |
| 6,004,892 A | 12/1999 | Guenther et al. | |
| 6,083,658 A * | 7/2000 | Kunita | G03F 7/0045 430/270.1 |
| 6,297,178 B1 | 10/2001 | Berbner et al. | |
| 6,822,030 B2 | 11/2004 | Olson et al. | |
| 6,884,557 B2 | 4/2005 | Kasai et al. | |
| 6,906,130 B2 | 6/2005 | Tutin et al. | |
| 7,008,994 B1 | 3/2006 | Waki | |
| 7,045,471 B2 | 5/2006 | Kobayashi | |
| 7,989,128 B2 | 8/2011 | Levy et al. | |
| 8,084,567 B2 | 12/2011 | Ogura et al. | |
| 2004/0225048 A1 | 11/2004 | Miura et al. | |
| 2004/0247882 A1 | 12/2004 | Kouchi et al. | |
| 2004/0258845 A1 | 12/2004 | Kasahara | |
| 2007/0134283 A1 | 6/2007 | Wang et al. | |
| 2008/0075999 A1 | 3/2008 | Izuhara et al. | |
| 2009/0304919 A1 | 12/2009 | Wagner et al. | |
| 2010/0164368 A1 | 7/2010 | Kong et al. | |
| 2010/0215922 A1 | 8/2010 | Rajaraman et al. | |
| 2010/0285309 A1 | 11/2010 | Barriau et al. | |
| 2010/0294429 A1 | 11/2010 | Hoevel | |
| 2011/0071056 A1 | 3/2011 | Saini et al. | |
| 2012/0164288 A1 | 6/2012 | Miller | |
| 2013/0190424 A1 | 7/2013 | Takamatsu et al. | |

FOREIGN PATENT DOCUMENTS

| | | |
|---|---|---|
| CN | 1259424 A | 7/2000 |
| CN | 1422881 A | 6/2003 |
| CN | 1631500 A | 6/2005 |
| CN | 1931852 A1 | 3/2007 |
| CN | 101245160 A | 8/2008 |
| CN | 102731768 A | 10/2012 |
| DE | 237512 A1 | 7/1986 |
| EP | 279475 A2 | 8/1988 |
| EP | 439259 A1 | 7/1991 |
| EP | 398749 B1 | 7/1995 |
| EP | 1122268 A1 | 8/2001 |
| EP | 1352888 A1 | 10/2003 |
| EP | 2149572 A1 | 2/2010 |
| JP | 55164267 A * | 12/1980 |
| JP | H05140138 A | 6/1993 |
| JP | 9304924 A | 11/1997 |
| JP | 2004020933 A | 1/2004 |
| SU | 1447816 A1 | 12/1988 |
| WO | 9303063 A1 | 2/1993 |
| WO | 9509200 A1 | 4/1995 |
| WO | 2002022332 A1 | 3/2002 |
| WO | 2005023744 A2 | 3/2005 |
| WO | 2010006350 A1 | 1/2010 |
| WO | WO2011/003446 A1 | 1/2011 |
| WO | 2012043245 A1 | 4/2012 |

OTHER PUBLICATIONS

Liu, Curing behavior and thermal properties of multifunctional epoxy resin with methylhexahydrophthalic anhydride, Journal of Applied Polymer Science (Feb. 2007), 103(3):2041-2048.

Thring, Catalytic Upgrading of a Solvolysis Lignin in a Batch Reactor, pp. 1-17.

World Epoxy Resin Market, Acmite Market Intelligence, pp. 1-12, (Oct. 2010).

Pan et al., Preparation of LMP 302 Aromatic Polyester, Polyurethane Industry (Apr. 30, 1991), (1) pp. 24-29.

Epoxy Resins, accessed at http://web.archive.org/web/20130124024338/http://info.smithersrapra.com/downloads/chapters/Thermoset%20Resins.pdf, accessed on Dec. 28, 2016, pp. 155-174.

Multi-Functional & Specialty Resins, accessed at http://web.archive.org/web/20120315052244/http://ww2.momentive.com/Products/Main.aspx?id=1058, accessed on Dec. 28, 2016, page 1.

Epoxy Resins, Aditya Birla Chemicals, accessed at http://web.archive.org/web120121215060508/http://www.adityabirlachemicals.com/productslepoxy_resins/epoxy_resins_overview.html, accessed on Dec. 28, 2016, Page.

Epoxy resins, Aditya Birla Chemicals, accessed at https://web.archive.org/webl20120422152558/htlp://www.adityabirlachemicals.com/products/epoxy_overview01.htm, accessed on Dec. 28, 2016, Pages 3.

Melamine, accessed at http//:web.archive.org/web/20130120085738/http://en.wikipedia.org/wiki/Melamine, last modified on Dec. 8, 2012, pp. 10.

Multifunctional, High Tg Epoxy Low-Flow Prepreg, accessed at http://web.archive.org/web/20120524083626/http://www.arlon-med.com/51N.pdf, accessed on Dec. 28, 2016, pp. 4.

Multifunctional, High Tg Epoxy Low-Flow Prepreg, accessed at http://streamlinecircuits.com/wpcontent/uploads/2015/08/51N.pdf, accessed on Dec. 30, 2016, pp. 4.

Phenolic Novolac And Resol Resins, Plenco, accessed at http://web.archive.org/web/20130110230432/htlp://www.plenco.com/phenolic-novolac-resol-resins.htm, accessed on Dec. 28, 2016, pp. 7.

Atta et al., Synthesis of Bisphenol A Novolac Epoxy Resins For Coating Applications, Journal of Applied Polymer Science (Sep. 19, 2007), 107(1) pp. 347-354.

Auchmoody et al., Effect of Calcium Cyanamide, On Growth and Nutrition of Planted Yellow-Poplar Seedlings (1973), USDA Forest Service Research Paper Ne-265, pp. 1-14.

Cech et al., The Effectiveness of Toughening Technologies on Multifunctional Epoxy Resin Systems, accessed at http://web.archive.org/web/20160519051151/http://www.hubronspeciality.com/ep-content/uploads/2013/09/CVC-TB-400-The-Effectiveness-of-Toughening-Technologies-on-Multifunctional-resin-systems.pdf, accessed on Dec. 30, 2016, pp. 15.

Ding et al., Synthesis and Adhesive Performances of Phenol Hydroxymethyl Acrylate (Jul. 30, 2003), Chemistry and Adhesion, pp. 159-164.

Extended European Search Report for European Application No. 13886810.4 dated Nov. 8, 2016.

Fitzgerald, Solution Behaviour of Polyethylene Oxide, Nonionic Gemini Surfactant, Ph.D Thesis (Dec., 2002) pp. 140.

Hesse et al., Phenolic Resins, Encyclpedia, of Industrial Chemistry (2012), (26) pp. 583-600.

International Search Report and Written Opinion for International Application No. PCT/US2012/062708 dated Jan. 9, 2013

International Search Report and Written Opinion for International Application No. PCT/US2013/045579 dated Dec. 2, 2013

International Search Report and Written Opinion for International Application No. PCT/US2013/072593 dated May 16, 2014.

International Search Report and Written Opinion for International Application No. PCT/US2013/072619 dated May 12, 2014

(56) References Cited

OTHER PUBLICATIONS

Liu et al., Halogen-free flame retardant epoxy resins from hybrids of phosphorus- or silicon-containing epoxies with an amine resin, Journal of Applied Polymer Science (Oct. 15, 2006), 102(2) pp. 1071-1077.
Lubczak, Polyhydroxyalkyl derivatives and polyetherols obtained from azacyclic compounds, Part II. Reactions with ormaldehyde and Alkylene Carbonates, Polimery, 56(6) pp. 452-460.
Mann, Self-assembly and transformation of hybrid nano-objects and nanostructures under equilibrium and non-equilibrium conditions, Nature Materials (Sep. 6, 2009), 8(10) pp. 781-792.
Pedroso et al., Melamine/epichlorohydrin prepolymers: syntheses and characterization, Polymer (Feb. 2005), 46(6) pp. 1766-1774.
Pilato, Resin Chemistry, Phenolic Resins: A Century of Progress (Feb. 27, 2010), Chapter-4, pp. 41-91.
Simon, Coatings odds and ends—From pinch tests to trade shows, accessed at https://web.archive.org/web/20120826140533/http://info.biocoat.com/?Tag=hydrophillic+coating+market, Posted on Feb. 23, 2012, pp. 5.
Simon, Lubricious Coatings in spec, on time, and on budget, accessed at https://web.archive.org/web/20120825102849/http://info.biocoat.com/?Tag=medical+device+coating, Posted on Aug. 13, 2012, pp. 6.
Swanson et al., Investigation of network development and properties in multifunctional epoxy resins using 3,3'-diaminodiphenylsulfone, accessed at http://www.trfa.org/Documents/Entry7-Swanson.pdf, accessed on Dec. 28, 2016, pp. 15.
Xia and Zana, Applications of Gemini Surfactants, Gemini Surfactants: Synthesis, Interfacial and Solution-Phase Behavior, and Applications, 2nd Edition(2004), (117)13, eds, Zana and Xia pp. 296-315.
Zaasshi et al., Formation of melamine and other cyanamide compounds by polymerization and condensation of dicyandiamide. IV. Proof of the formation of 2,4,6-trimethyl-s-triazine, Journal of the Society of Chemical Industry (May 31, 1968), 71(5) pp. 727-732. (English Abstract).
Fields, D.L., et al. "Mannich-type Condensation of Hydroquinone, Formaldehyde and Primary Amines,"The Journal of Organic Chemistry, Vol. 27, No. 8, pp. 2749-2753 (Aug. 1962)
Partial Supplementary European Search Report for European Application No. 138985346 dated Jun. 27, 2017, pp. 16.
Rakhimova, E.B., et al., "New Methods for the Synthesis of αωBIS-1,5,3-Dithiazepanes on the Basis of Aliphatic α,ω-Diamines," Chemistry of Heterocyclic Compounds, vol. 49, No. 8, pp. 1237-1242 (Aug. 2013)
Partial Supplementary European Search Report for European Application No. 138988472 dated Jul. 5, 2017, pp. 13
Ricci, C.G., "Micellar-lmproved Synthesis of Bis-quatemary Ammonium Salts by the Epichlorohydrin Route" Journal of Surfactants and Detergents, vol. 06, No. 03, pp. 231-237 (Jul. 2003).
STN Columbus, Registry No. 70914-27-1, Entered on Aug. 2, 2017, pp. 3.
Liang, et al., "The Synthesis Progress of Chelating Surfactant Derivatives of EDTA," Fine Chemical Intermediates, vol. 34, No. 5, pp. 03 (Oct. 30, 2004)(English abstract).

* cited by examiner

PHENOLIC EPOXY COMPOUNDS

CROSS-REFERENCE TO RELATED APPLICATION

This application is a U.S. national stage filing under 35 U.S.C. § 371 of International Application No. PCT/US2013/071204 filed on Nov. 21, 2013, which claims the benefit of and priority to U.S. Provisional Application Ser. No. 61/765,324, entitled "Phenolic Epoxy Compounds," which was filed on Feb. 15, 2013. The aforementioned applications are incorporated by reference herein in its entirety and for all purposes.

BACKGROUND

An important part of many manufacturing operations is the joining of structures that are separately prepared into larger pieces, which may themselves be joined to other structures or may be the final assembled parts. Joining of structures is a critical operation because subsequent failures may occur at the locations where structures are joined or because there may be special requirements to be met at the interface between two structures. The surface along which two structures are joined must therefore be strong, resistant to failure by many different mechanisms, such as fatigue and corrosion, and additionally meet other requirements. Epoxy resins and their composites are routinely used in joining structures in manufacturing industries to achieve these goals.

Multifunctional epoxy resins are the backbone of the rapidly growing aerospace and composite industries. In addition, epoxy resins are also used in encapsulating semiconductors, in coatings, in paints, and in forming Interpenetrating Polymer Networks (IPNs). The degree of functionality (number of epoxy groups per molecule) of an epoxy resin is critical in determining its final properties and its end-use applications. In addition, the cost of the monomer production and the viscosity of the resin also influence its applicability. Accordingly, there is a need for the production of new resins with enhanced functionality and improved toughness which can be used in a wide variety of industrial applications.

SUMMARY

The present disclosure is directed to phenolic compounds and resins comprising these phenolic compounds. In one embodiment, a compound is of formula I

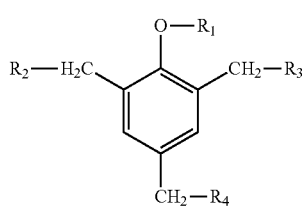

wherein:
$R_1$ is H or Z;
$R_2$ is —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, OH, NH$_2$, —O—Z, —CH$_2$—O—Z, —CH$_2$CH$_2$—O—Z, —CH$_2$OH, —CH$_2$NH$_2$, —O—C—(CH$_3$)$_3$, —O-(alkylene)-CH$_3$;
$R_3$ is —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, OH, NH$_2$, —O—Z, —CH$_2$—O—Z, —CH$_2$CH$_2$—O—Z, —CH$_2$OH, —CH$_2$NH$_2$, —O—C—(CH$_3$)$_3$, or —O-(alkylene)-CH$_3$;
$R_4$ is —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, OH, NH$_2$, —O—Z, —CH$_2$—O—Z, —CH$_2$CH$_2$—O—Z, —CH$_2$OH, —CH$_2$NH$_2$, —O—C—(CH$_3$)$_3$, or —O-(alkylene)-CH$_3$; and
Z is

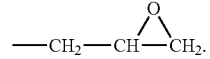

In another embodiment, a compound is of formula II

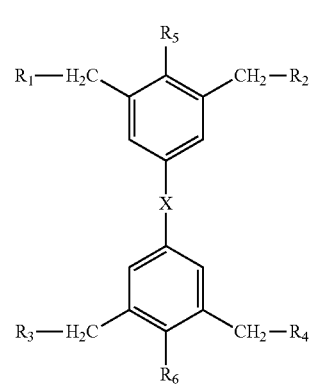

wherein:
X is —CH$_2$—, —C(CH$_3$)$_2$—, —S—, —S(=O)$_2$—, —S(=O)—, —CH(CCl$_3$)—, —C(Cl)$_2$—, or —C(F)$_2$—;
$R_1$ is OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$;
$R_2$ is OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$;
$R_3$ is OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$;
$R_4$ is OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$;
$R_5$ is OH or —O—Z;
$R_6$ is OH or —O—Z;
Z is

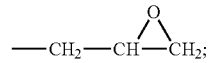

and
Y is Cl, Br, F, or I.

In an additional embodiment, a composition may include any one or more of the compounds of formula I or formula II as described herein.

In a further embodiment, an article of manufacture, such as an aerospace, an automobile, or a sporting good article of manufacture, may include any one or more of the compounds of formula I and/or formula II as described herein.

In another embodiment, a method of preparing a compound may include: (a) contacting a phenolic compound with a formaldehyde or paraformaldehyde to form a hydroxymethyl compound; and (b) contacting the hydroxymethyl compound with an epihalohydrin compound, a diethanolamine compound, or an ammonia, to form the compound.

DETAILED DESCRIPTION

This disclosure is not limited to the particular systems, devices and methods described, as these may vary. The terminology used in the description is for the purpose of describing the particular versions or embodiments only, and is not intended to limit the scope.

As used herein, "alkylene" refers to a bivalent alkyl moiety having the general formula $-(CH_2)_n-$, where n is from about 1 to about 25, or about 1 to about 20, or about 4 to about 20. By bivalent, it is meant that the group has two open sites each of which bonds to another group. Non-limiting examples include methylene, ethylene, trimethylene, pentamethylene, and hexamethylene. Alkylene groups can be substituted or unsubstituted, linear or a branched bivalent alkyl groups.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (for example, n-propyl and isopropyl), butyl (for example, n-butyl, t-butyl, isobutyl), pentyl (for example, n-pentyl, isopentyl, neopentyl), hexyl, isohexyl, heptyl, 4,4 dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

"Substituted alkyl" refers to an alkyl as just described in which one or more hydrogen atoms attached to carbon of the alkyl is replaced by another group, such as halogen, aryl, substituted aryl, cycloalkyl, substituted cycloalkyl, and combinations thereof. Suitable substituted alkyls include, for example, benzyl and trifluoromethyl.

Disclosed herein are compositions and methods for making phenolic compounds that may be incorporated in, for example, resins. In some embodiments, the phenolic compound is of formula I

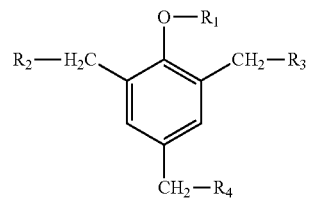

In some embodiments, $R_1$ may be H or Z. Z is glycidyl group represented by

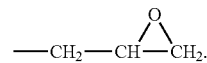

In some embodiments, $R_1$ may be Z.

In some embodiments, $R_2$ may be selected from $-N(Z)_2$, $-N(CH_2-O-Z)_2$, $-N(CH_2CH_2-O-Z)_2$, $-N(CH_2OH)_2$, $-N(CH_2NH_2)_2$, $-N(CH_2CH_2OH)_2$, OH, $NH_2$, $-O-Z$, $-CH_2-O-Z$, $-CH_2CH_2-O-Z$, $-CH_2OH$, $-CH_2NH_2$, $-O-C-(CH_3)_3$, or $-O$-(alkylene)-$CH_3$. In some embodiments, $R_2$ may be $-N(Z)_2$, $-N(CH_2-O-Z)_2$, $-N(CH_2CH_2-O-Z)_2$, $-N(CH_2OH)_2$, $-N(CH_2NH_2)_2$, $-N(CH_2CH_2OH)_2$, OH, $NH_2$, $-O-Z$, $-CH_2-O-Z$, $-CH_2CH_2-O-Z$, or $-CH_2OH$. In some embodiments, $R_2$ may be $-N(Z)_2$, $-N(CH_2-O-Z)_2$, $-N(CH_2CH_2-O-Z)_2$, $-N(CH_2OH)_2$, $-N(CH_2NH_2)_2$, $-N(CH_2CH_2OH)_2$, OH, $NH_2$, or $-O-Z$.

In some embodiments, $R_3$ may be selected from $-N(Z)_2$, $-N(CH_2-O-Z)_2$, $-N(CH_2CH_2-O-Z)_2$, $-N(CH_2OH)_2$, $-N(CH_2NH_2)_2$, $-N(CH_2CH_2OH)_2$, OH, $NH_2$, $-O-Z$, $-CH_2-O-Z$, $-CH_2CH_2-O-Z$, $-CH_2OH$, $-CH_2NH_2$, $-O-C-(CH_3)_3$, or $-O$-(alkylene)-$CH_3$. In some embodiments, $R_3$ may be $-N(Z)_2$, $-N(CH_2-O-Z)_2$, $-N(CH_2CH_2-O-Z)_2$, $-N(CH_2OH)_2$, $-N(CH_2NH_2)_2$, $-N(CH_2CH_2OH)_2$, OH, $NH_2$, $-O-Z$, $-CH_2-O-Z$, $-CH_2CH_2-O-Z$, $-CH_2OH$, or $-CH_2NH_2$. In some embodiments, $R_3$ may be $-N(Z)_2$, $-N(CH_2-O-Z)_2$, $-N(CH_2CH_2-O-Z)_2$, $-N(CH_2OH)_2$, $-N(CH_2NH_2)_2$, $-N(CH_2CH_2OH)_2$, OH, $NH_2$, $-O-Z$, $-CH_2-O-Z$, or $-CH_2CH_2-O-Z$.

In some embodiments, $R_4$ may be $-N(Z)_2$, $-N(CH_2-O-Z)_2$, $-N(CH_2CH_2-O-Z)_2$, $-N(CH_2OH)_2$, $-N(CH_2NH_2)_2$, $-N(CH_2CH_2OH)_2$, OH, $NH_2$, $-O-Z$, $-CH_2-O-Z$, $-CH_2CH_2-O-Z$, $-CH_2OH$, $-CH_2NH_2$, $-O-C-(CH_3)_3$, or $-O$-(alkylene)-$CH_3$. In some embodiments, $R_4$ may be $-N(Z)_2$, $-N(CH_2-O-Z)_2$, $-N(CH_2CH_2-O-Z)_2$, $-N(CH_2OH)_2$, $-N(CH_2NH_2)_2$, $-N(CH_2CH_2OH)_2$, OH, $NH_2$, $-O-Z$, $-CH_2-O-Z$, $-CH_2CH_2-O-Z$, or $-CH_2OH$. In some embodiments, $R_4$ may be $-N(Z)_2$, $-N(CH_2-O-Z)_2$, $-N(CH_2CH_2-O-Z)_2$, $-N(CH_2OH)_2$, $-N(CH_2NH_2)_2$, $-N(CH_2CH_2OH)_2$, OH, $NH_2$, or $-O-Z$.

In some embodiments, the compound of formula I may have the following substitutions at $R_1$, $R_2$, $R_3$ and $R_4$, as shown in Table 1:

TABLE 1

| $R_1$ | $R_2$ | $R_3$ | $R_4$ |
|---|---|---|---|
| H | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$,<br>—N(CH$_2$CH$_2$OH)$_2$,<br>—OH,<br>—NH$_2$,<br>—O—Z,<br>—CH$_2$—O—Z,<br>—CH$_2$CH$_2$—O—Z,<br>—CH$_2$OH,<br>—CH$_2$NH$_2$,<br>—O—C—(CH$_3$)$_3$, or<br>—O-(alkylene)-CH$_3$. | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$,<br>—N(CH$_2$CH$_2$OH)$_2$,<br>—OH,<br>—NH$_2$,<br>—O—Z,<br>—CH$_2$—O—Z,<br>—CH$_2$CH$_2$—O—Z,<br>—CH$_2$OH,<br>—CH$_2$NH$_2$,<br>—O—C—(CH$_3$)$_3$, or<br>—O-(alkylene)-CH$_3$. | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$,<br>—N(CH$_2$CH$_2$OH)$_2$,<br>—OH,<br>—NH$_2$,<br>—O—Z,<br>—CH$_2$—O—Z,<br>—CH$_2$CH$_2$—O—Z,<br>—CH$_2$OH,<br>—CH$_2$NH$_2$,<br>—O—C—(CH$_3$)$_3$, or<br>—O-(alkylene)-CH$_3$. |
| H | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$, or<br>—N(CH$_2$CH$_2$OH)$_2$. | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$, or<br>—N(CH$_2$CH$_2$OH)$_2$. | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$, or<br>—N(CH$_2$CH$_2$OH)$_2$. |
| H | —N(Z)$_2$,<br>—N(CH$_2$—O—Z)$_2$, or<br>—N(CH$_2$—CH$_2$—O—Z)$_2$. | —N(Z)$_2$,<br>—N(CH$_2$—O—Z)$_2$, or<br>—N(CH$_2$—CH$_2$—O—Z)$_2$. | —N(Z)$_2$,<br>—N(CH$_2$—O—Z)$_2$, or<br>—N(CH$_2$—CH$_2$—O—Z)$_2$. |
| H | —N(CH$_2$OH)$_2$,<br>—N(CH$_2$NH$_2$)$_2$, or<br>—N(CH$_2$CH$_2$OH)$_2$. | —N(CH$_2$OH)$_2$,<br>—N(CH$_2$NH$_2$)$_2$, or<br>—N(CH$_2$CH$_2$OH)$_2$. | —N(CH$_2$OH)$_2$,<br>—N(CH$_2$NH$_2$)$_2$, or<br>—N(CH$_2$CH$_2$OH)$_2$. |
| H | —O—C—(CH$_3$)$_3$, or<br>—O—(CH$_2$)$_{10}$—CH$_3$. | —O—C—(CH$_3$)$_3$, or<br>—O—(CH$_2$)$_{10}$—CH$_3$. | —O—C—(CH$_3$)$_3$, or<br>—O—(CH$_2$)$_{10}$—CH$_3$. |
| H | —N(Z)$_2$ | —N(Z)$_2$ | —N(Z)$_2$ |
| H | —N(CH$_2$—O—Z)$_2$ | —N(CH$_2$—O—Z)$_2$ | —N(CH$_2$—O—Z)$_2$ |
| H | —N(CH$_2$CH$_2$—O—Z)$_2$ | —N(CH$_2$CH$_2$—O—Z)$_2$ | —N(CH$_2$CH$_2$—O—Z)$_2$ |
| H | —N(CH$_2$OH)$_2$ | —N(CH$_2$OH)$_2$ | —N(CH$_2$OH)$_2$ |
| H | —N(CH$_2$NH$_2$)$_2$ | —N(CH$_2$NH$_2$)$_2$ | —N(CH$_2$NH$_2$)$_2$ |
| H | —N(CH$_2$CH$_2$OH)$_2$ | —N(CH$_2$CH$_2$OH)$_2$ | —N(CH$_2$CH$_2$OH)$_2$ |
| H | —O—Z | —O—Z | —O—Z |
| H | —O—C—(CH$_3$)$_3$ | —O—C—(CH$_3$)$_3$ | —O—C—(CH$_3$)$_3$ |
| H | —O—(CH$_2$)$_{10}$—CH$_3$. | —O—(CH$_2$)$_{10}$—CH$_3$. | —O—(CH$_2$)$_{10}$—CH$_3$. |

In some embodiments, compounds of formula I may have the following substitutions at $R_1$, $R_2$, $R_3$ and $R_4$, as shown in Table 2:

TABLE 2

| $R_1$ | $R_2$ | $R_3$ | $R_4$ |
|---|---|---|---|
| Z | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$,<br>—N(CH$_2$CH$_2$OH)$_2$,<br>—OH,<br>—NH$_2$,<br>—O—Z,<br>—CH$_2$—O—Z,<br>—CH$_2$CH$_2$—O—Z,<br>—CH$_2$OH,<br>—CH$_2$NH$_2$,<br>—O—C—(CH$_3$)$_3$, or<br>—O-(alkylene)-CH$_3$. | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$,<br>—N(CH$_2$CH$_2$OH)$_2$,<br>—OH,<br>—NH$_2$,<br>—O—Z,<br>—CH$_2$—O—Z,<br>—CH$_2$CH$_2$—O—Z,<br>—CH$_2$OH,<br>—CH$_2$NH$_2$,<br>—O—C—(CH$_3$)$_3$, or<br>—O-(alkylene)-CH$_3$. | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$,<br>—N(CH$_2$CH$_2$OH)$_2$,<br>—OH,<br>—NH$_2$,<br>—O—Z,<br>—CH$_2$—O—Z,<br>—CH$_2$CH$_2$—O—Z,<br>—CH$_2$OH,<br>—CH$_2$NH$_2$,<br>—O—C—(CH$_3$)$_3$, or<br>—O-(alkylene)-CH$_3$. |
| Z | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$, or<br>—N(CH$_2$CH$_2$OH)$_2$. | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$, or<br>—N(CH$_2$CH$_2$OH)$_2$. | —N(Z)$_2$,<br>—N(CH$_2$—O—Z)$_2$,<br>—N(CH$_2$—CH$_2$—O—Z)$_2$,<br>—N(CH$_2$OH)$_2$,<br>—N(CH$_2$NH$_2$)$_2$, or<br>—N(CH$_2$CH$_2$OH)$_2$. |
| Z | —N(Z)$_2$,<br>—N(CH$_2$—O—Z)$_2$, or<br>—N(CH$_2$—CH$_2$—O—Z)$_2$. | —N(Z)$_2$,<br>—N(CH$_2$—O—Z)$_2$, or<br>—N(CH$_2$—CH$_2$—O—Z)$_2$. | —N(Z)$_2$,<br>—N(CH$_2$—O—Z)$_2$, or<br>—N(CH$_2$—CH$_2$—O—Z)$_2$. |

TABLE 2-continued

| $R_1$ | $R_2$ | $R_3$ | $R_4$ |
|---|---|---|---|
| Z | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. |
| Z | —O—C—(CH$_3$)$_3$, or —O—(CH$_2$)$_{10}$—CH$_3$. | —O—C—(CH$_3$)$_3$, or —O—(CH$_2$)$_{10}$—CH$_3$. | —O—C—(CH$_3$)$_3$, or —O—(CH$_2$)$_{10}$—CH$_3$. |
| Z | —N(Z)$_2$ | —N(Z)$_2$ | —N(Z)$_2$ |
| Z | —N(CH$_2$—O—Z)$_2$ | —N(CH$_2$—O—Z)$_2$ | —N(CH$_2$—O—Z)$_2$ |
| Z | —N(CH$_2$CH$_2$—O—Z)$_2$ | —N(CH$_2$CH$_2$—O—Z)$_2$ | —N(CH$_2$CH$_2$—O—Z)$_2$ |
| Z | —N(CH$_2$OH)$_2$ | —N(CH$_2$OH)$_2$ | —N(CH$_2$OH)$_2$ |
| Z | —N(CH$_2$NH$_2$)$_2$ | —N(CH$_2$NH$_2$)$_2$ | —N(CH$_2$NH$_2$)$_2$ |
| Z | —N(CH$_2$CH$_2$OH)$_2$ | —N(CH$_2$CH$_2$OH)$_2$ | —N(CH$_2$CH$_2$OH)$_2$ |
| Z | —O—Z | —O—Z | —O—Z |
| Z | —O—C—(CH$_3$)$_3$ | —O—C—(CH$_3$)$_3$ | —O—C—(CH$_3$)$_3$ |
| Z | —O—(CH$_2$)$_{10}$—CH$_3$. | —O—(CH$_2$)$_{10}$—CH$_3$. | —O—(CH$_2$)$_{10}$—CH$_3$. |

Non-limiting examples of phenolic compounds represented by formula I include, but are not limited to, the following compounds:

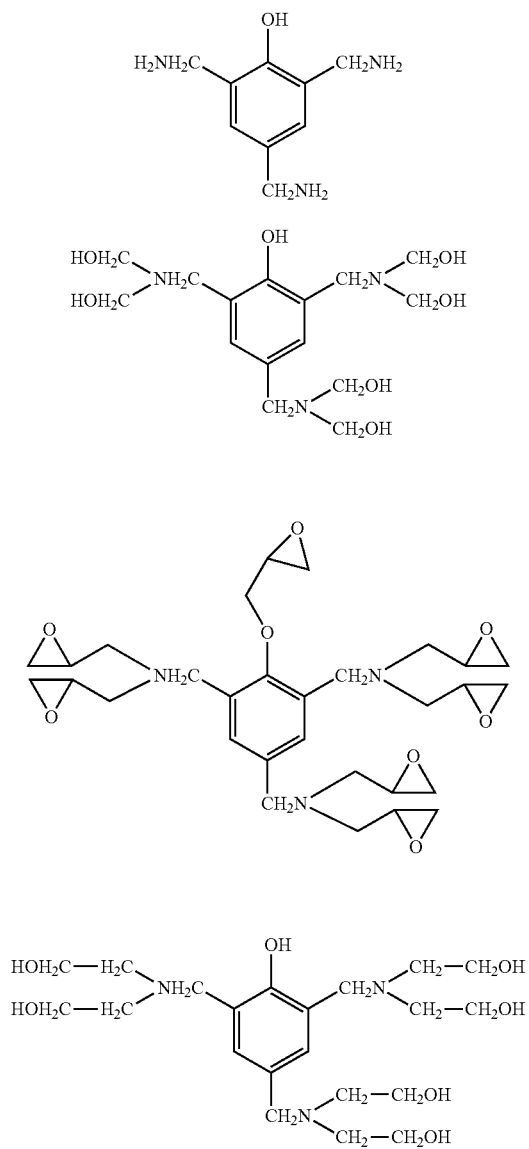

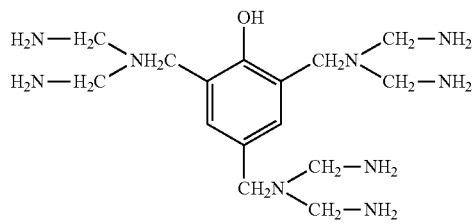

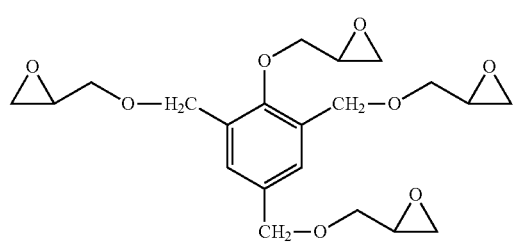

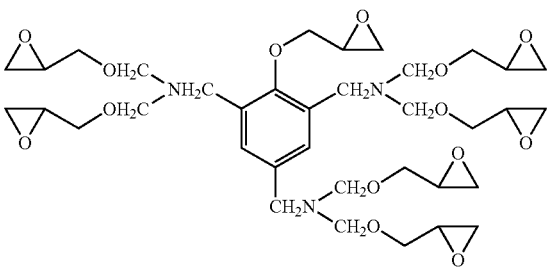

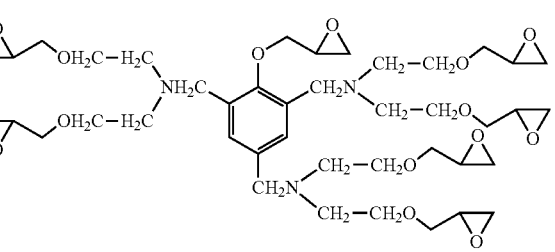

In some embodiments, the phenolic compound is of formula II

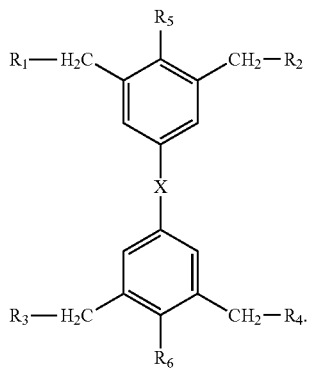

In some embodiments, X may be —CH$_2$—, —C(CH$_3$)$_2$—, —S—, —S(=O)$_2$—, —S(=O)—, —CH(CCl$_3$)—, —C(Cl)$_2$—, or —C(F)$_2$—. In some embodiments, X may be —CH$_2$—, —C(CH$_3$)$_2$—, —S—, —S(=O)$_2$—, —S(=O)—, or —CH(CCl$_3$)—. In some embodiments, X may be —CH$_2$—, —C(CH$_3$)$_2$—, —S—, or —S(=O)$_2$—.

In some embodiments, R$_1$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. In some embodiments, R$_1$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, or —CH$_2$NH$_2$. In some embodiments, R$_1$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, or —CH$_2$—O—Z.

In some embodiments, R$_2$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. In some embodiments, R$_2$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, or —CH$_2$NH$_2$. In some embodiments, R$_2$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, or —CH$_2$—O—Z.

In some embodiments, R$_3$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. In some embodiments, R$_3$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, or —CH$_2$NH$_2$. In some embodiments, R$_3$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, or NH$_2$.

In some embodiments, R$_4$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. In some embodiments, R$_4$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, —CH$_2$—O—Z, —CH$_2$CH$_2$—O—Z, —CH$_2$OH, or —CH$_2$NH$_2$. In some embodiments, R$_4$ may be OH, —O—Z, —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —N(CH$_2$CH$_2$OH)$_2$, NH$_2$, or —CH$_2$—O—Z.

In some embodiments, R$_5$ is OH, or —O—Z.

In some embodiments, R$_6$ is OH, or —O—Z. Z is

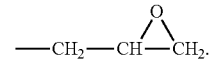

In some embodiments, Y is Cl, Br, F, or I.

In some embodiments, compounds of formula II may have the following substitutions at each of, independently, X, R$_1$, R$_2$, R$_3$, R$_4$, R$_5$ and R$_6$, as shown in Table 3:

TABLE 3

| X | R$_1$ | R$_2$ | R$_3$ | R$_4$ | R$_5$ | R$_6$ |
|---|---|---|---|---|---|---|
| —CH$_2$— | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, or —O—Z. | —OH, or —O—Z. |
| —CH$_2$— | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —OH, or —O—Z. | —OH, or —O—Z. |

TABLE 3-continued

| X | $R_1$ | $R_2$ | $R_3$ | $R_4$ | $R_5$ | $R_6$ |
|---|---|---|---|---|---|---|
| —$CH_2$— | —$N(Z)_2$, —$N(CH_2$—O—$Z)_2$, or —$N(CH_2$—$CH_2$—O—$Z)_2$. | —$N(Z)_2$, —$N(CH_2$—O—$Z)_2$, or —$N(CH_2$—$CH_2$—O—$Z)_2$. | —$N(Z)_2$, —$N(CH_2$—O—$Z)_2$, or —$N(CH_2$—$CH_2$—O—$Z)_2$. | —$N(Z)_2$, —$N(CH_2$—O—$Z)_2$, or —$N(CH_2$—$CH_2$—O—$Z)_2$. | —OH, or —O—Z. | —OH, or —O—Z. |
| —$CH_2$— | —$N(CH_2OH)_2$, —$N(CH_2NH_2)_2$, or —$N(CH_2CH_2OH)_2$. | —$N(CH_2OH)_2$, —$N(CH_2NH_2)_2$, or —$N(CH_2CH_2OH)_2$. | —$N(CH_2OH)_2$, —$N(CH_2NH_2)_2$, or —$N(CH_2CH_2OH)_2$. | —$N(CH_2OH)_2$, —$N(CH_2NH_2)_2$, or —$N(CH_2CH_2OH)_2$. | —OH, or —O—Z. | —OH, or —O—Z. |
| —$CH_2$— | —O—C—$(CH_3)_3$, or —O—$(CH_2)_{10}$—$CH_3$. | —O—C—$(CH_3)_3$, or —O—$(CH_2)_{10}$—$CH_3$. | —O—C—$(CH_3)_3$, or —O—$(CH_2)_{10}$—$CH_3$. | —O—C—$(CH_3)_3$, or —O—$(CH_2)_{10}$—$CH_3$. | —OH, or —O—Z. | —OH, or —O—Z. |
| —$CH_2$— | —$N(Z)_2$ | —$N(Z)_2$ | —$N(Z)_2$ | —$N(Z)_2$ | —O—Z | —O—Z |
| —$CH_2$— | —$N(CH_2$—O—$Z)_2$ | —$N(CH_2$—O—$Z)_2$ | —$N(CH_2$—O—$Z)_2$ | —$N(CH_2$—O—$Z)_2$ | —O—Z | —O—Z |
| —$CH_2$— | —$N(CH_2CH_2$—O—$Z)_2$ | —$N(CH_2CH_2$—O—$Z)_2$ | —$N(CH_2CH_2$—O—$Z)_2$ | —$N(CH_2CH_2$—O—$Z)_2$ | —O—Z | —O—Z |
| —$CH_2$— | —$N(CH_2OH)_2$ | —$N(CH_2OH)_2$ | —$N(CH_2OH)_2$ | —$N(CH_2OH)_2$ | —OH | —OH |
| —$CH_2$— | —$N(CH_2NH_2)_2$ | —$N(CH_2NH_2)_2$ | —$N(CH_2NH_2)_2$ | —$N(CH_2NH_2)_2$ | —OH | —OH |
| —$CH_2$— | —$N(CH_2CH_2OH)_2$ | —$N(CH_2CH_2OH)_2$ | —$N(CH_2CH_2OH)_2$ | —$N(CH_2CH_2OH)_2$ | —OH | —OH |
| —$CH_2$— | —O—Z | —O—Z | —O—Z | —O—Z | —O—Z | —O—Z |
| —$CH_2$— | —O—C—$(CH_3)_3$ | —O—C—$(CH_3)_3$ | —O—C—$(CH_3)_3$ | —O—C—$(CH_3)_3$ | —OH | —OH |
| —$CH_2$— | —O—$(CH_2)_{10}$—$CH_3$. | —O—$(CH_2)_{10}$—$CH_3$. | —O—$(CH_2)_{10}$—$CH_3$. | —O—$(CH_2)_{10}$—$CH_3$. | —OH | —OH |
| —$CH_2$— | —OH or —O—Z | —OH or —O—Z | —OH or —O—Z | —OH or —O—Z | —OH or —O—Z | —OH or —O—Z |
| —$CH_2$— | —OH | —OH | —OH | —OH | —OH | —OH |

In some embodiments, compounds of formula II may have the following substitutions at each or, independently, X, $R_1$, $R_2$, $R_3$, $R_4$, $R_5$ and $R_6$, as shown in Table 4:

TABLE 4

| X | $R_1$ | $R_2$ | $R_3$ | $R_4$ | $R_5$ | $R_6$ |
|---|---|---|---|---|---|---|
| —$C(CH_3)_2$— | —OH, —O—Z, —$N(Z)_2$, —$N(CH_2$—O—$Z)_2$, —$N(CH_2$—$CH_2$—O—$Z)_2$, —$N(CH_2OH)_2$, —$N(CH_2NH_2)_2$, —$N(CH_2CH_2OH)_2$, —$NH_2$, —$CH_2$—O—Z, —$CH_2CH_2$—O—Z, —$CH_2OH$, —$CH_2NH_2$, —$CH_2$—Y, —O—C—$(CH_3)_3$, or —O-(alkylene)-$CH_3$. | —OH, —O—Z, —$N(Z)_2$, —$N(CH_2$—O—$Z)_2$, —$N(CH_2$—$CH_2$—O—$Z)_2$, —$N(CH_2OH)_2$, —$N(CH_2NH_2)_2$, —$N(CH_2CH_2OH)_2$, —$NH_2$, —$CH_2$—O—Z, —$CH_2CH_2$—O—Z, —$CH_2OH$, —$CH_2NH_2$, —$CH_2$—Y, —O—C—$(CH_3)_3$, or —O-(alkylene)-$CH_3$. | —OH, —O—Z, —$N(Z)_2$, —$N(CH_2$—O—$Z)_2$, —$N(CH_2$—$CH_2$—O—$Z)_2$, —$N(CH_2OH)_2$, —$N(CH_2NH_2)_2$, —$N(CH_2CH_2OH)_2$, —$NH_2$, —$CH_2$—O—Z, —$CH_2CH_2$—O—Z, —$CH_2OH$, —$CH_2NH_2$, —$CH_2$—Y, —O—C—$(CH_3)_3$, or —O-(alkylene)-$CH_3$. | —OH, —O—Z, —$N(Z)_2$, —$N(CH_2$—O—$Z)_2$, —$N(CH_2$—$CH_2$—O—$Z)_2$, —$N(CH_2OH)_2$, —$N(CH_2NH_2)_2$, —$N(CH_2CH_2OH)_2$, —$NH_2$, —$CH_2$—O—Z, —$CH_2CH_2$—O—Z, —$CH_2OH$, —$CH_2NH_2$, —$CH_2$—Y, —O—C—$(CH_3)_3$, or —O-(alkylene)-$CH_3$. | —OH, or —O—Z. | —OH, or —O—Z. |
| —$C(CH_3)_2$— | —$N(Z)_2$, —$N(CH_2$—O—$Z)_2$, —$N(CH_2$—$CH_2$—O—$Z)_2$, —$N(CH_2OH)_2$, —$N(CH_2NH_2)_2$, or —$N(CH_2CH_2OH)_2$. | —$N(Z)_2$, —$N(CH_2$—O—$Z)_2$, —$N(CH_2$—$CH_2$—O—$Z)_2$, —$N(CH_2OH)_2$, —$N(CH_2NH_2)_2$, or —$N(CH_2CH_2OH)_2$. | —$N(Z)_2$, —$N(CH_2$—O—$Z)_2$, —$N(CH_2$—$CH_2$—O—$Z)_2$, —$N(CH_2OH)_2$, —$N(CH_2NH_2)_2$, or —$N(CH_2CH_2OH)_2$. | —$N(Z)_2$, —$N(CH_2$—O—$Z)_2$, —$N(CH_2$—$CH_2$—O—$Z)_2$, —$N(CH_2OH)_2$, —$N(CH_2NH_2)_2$, or —$N(CH_2CH_2OH)_2$. | —OH, or —O—Z. | —OH, or —O—Z. |
| —$C(CH_3)_2$— | —$N(Z)_2$, —$N(CH_2$—O—$Z)_2$, or —$N(CH_2$—$CH_2$—O—$Z)_2$. | —$N(Z)_2$, —$N(CH_2$—O—$Z)_2$, or —$N(CH_2$—$CH_2$—O—$Z)_2$. | —$N(Z)_2$, —$N(CH_2$—O—$Z)_2$, or —$N(CH_2$—$CH_2$—O—$Z)_2$. | —$N(Z)_2$, —$N(CH_2$—O—$Z)_2$, or —$N(CH_2$—$CH_2$—O—$Z)_2$. | —OH, or —O—Z. | —OH, or —O—Z. |
| —$C(CH_3)_2$— | —$N(CH_2OH)_2$, —$N(CH_2NH_2)_2$, or —$N(CH_2CH_2OH)_2$. | —$N(CH_2OH)_2$, —$N(CH_2NH_2)_2$, or —$N(CH_2CH_2OH)_2$. | —$N(CH_2OH)_2$, —$N(CH_2NH_2)_2$, or —$N(CH_2CH_2OH)_2$. | —$N(CH_2OH)_2$, —$N(CH_2NH_2)_2$, or —$N(CH_2CH_2OH)_2$. | —OH, or —O—Z. | —OH, or —O—Z. |
| —$C(CH_3)_2$— | —O—C—$(CH_3)_3$, or —O—$(CH_2)_{10}$—$CH_3$. | —O—C—$(CH_3)_3$, or —O—$(CH_2)_{10}$—$CH_3$ | —O—C—$(CH_3)_3$, or —O—$(CH_2)_{10}$—$CH_3$. | —O—C—$(CH_3)_3$, or —O—$(CH_2)_{10}$—$CH_3$ | —OH, or —O—Z. | —OH, or —O—Z. |
| —$C(CH_3)_2$— | —$N(Z)_2$ | —$N(Z)_2$ | —$N(Z)_2$ | —$N(Z)_2$ | —O—Z | —O—Z |
| —$C(CH_3)_2$— | —$N(CH_2$—O—$Z)_2$ | —$N(CH_2$—O—$Z)_2$ | —$N(CH_2$—O—$Z)_2$ | —$N(CH_2$—O—$Z)_2$ | —O—Z | —O—Z |
| —$C(CH_3)_2$— | —$N(CH_2CH_2$—O—$Z)_2$ | —$N(CH_2CH_2$—O—$Z)_2$ | —$N(CH_2CH_2$—O—$Z)_2$ | —$N(CH_2CH_2$—O—$Z)_2$ | —O—Z | —O—Z |
| —$C(CH_3)_2$— | —$N(CH_2OH)_2$ | —$N(CH_2OH)_2$ | —$N(CH_2OH)_2$ | —$N(CH_2OH)_2$ | —OH | —OH |
| —$C(CH_3)_2$— | —$N(CH_2NH_2)_2$ | —$N(CH_2NH_2)_2$ | —$N(CH_2NH_2)_2$ | —$N(CH_2NH_2)_2$ | —OH | —OH |
| —$C(CH_3)_2$— | —$N(CH_2CH_2OH)_2$ | —$N(CH_2CH_2OH)_2$ | —$N(CH_2CH_2OH)_2$ | —$N(CH_2CH_2OH)_2$ | —OH | —OH |
| —$C(CH_3)_2$— | —O—Z | —O—Z | —O—Z | —O—Z | —O—Z | —O—Z |
| —$C(CH_3)_2$— | —O—C—$(CH_3)_3$ | —O—C—$(CH_3)_3$ | —O—C—$(CH_3)_3$ | —O—C—$(CH_3)_3$ | —OH | —OH |

TABLE 4-continued

| X | $R_1$ | $R_2$ | $R_3$ | $R_4$ | $R_5$ | $R_6$ |
|---|---|---|---|---|---|---|
| —C(CH$_3$)$_2$— | —O—(CH$_2$)$_{10}$—CH$_3$ | —O—(CH$_2$)$_{10}$—CH$_3$ | —O—(CH$_2$)$_{10}$—CH$_3$ | —O—(CH$_2$)$_{10}$—CH$_3$ | —OH | —OH |
| —C(CH$_3$)$_2$— | —OH or —O—Z | —OH or —O—Z | —OH or —O—Z | —OH or —O—Z | —OH or —O—Z | —OH or —O—Z |
| —C(CH$_3$)$_2$— | —OH | —OH | —OH | —OH | —OH | —OH |

In some embodiments, compounds of formula II may have the following substitutions at each of, independently, X, $R_1$, $R_2$, $R_3$, $R_4$, $R_5$ and $R_6$, as shown in Table 5:

TABLE 5

| X | $R_1$ | $R_2$ | $R_3$ | $R_4$ | $R_5$ | $R_6$ |
|---|---|---|---|---|---|---|
| —S— | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, or —O—Z. | —OH, or —O—Z. |
| —S— | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —OH, or —O—Z. | —OH, or —O—Z. |
| —S— | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —OH, or —O—Z. | —OH, or —O—Z. |
| —S— | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —OH, or —O—Z. | —OH, or —O—Z. |
| —S— | —O—C—(CH$_3$)$_3$, or —O—(CH$_2$)$_{10}$—CH$_3$. | —O—C—(CH$_3$)$_3$, or —O—(CH$_2$)$_{10}$—CH$_3$. | —O—C—(CH$_3$)$_3$, or —O—(CH$_2$)$_{10}$—CH$_3$. | —O—C—(CH$_3$)$_3$, or —O—(CH$_2$)$_{10}$—CH$_3$. | —OH, or —O—Z. | —OH, or —O—Z. |
| —S— | —N(Z)$_2$ | —N(Z)$_2$ | —N(Z)$_2$ | —N(Z)$_2$ | —O—Z | —O—Z |
| —S— | —N(CH$_2$—O—Z)$_2$ | —N(CH$_2$—O—Z)$_2$ | —N(CH$_2$—O—Z)$_2$ | —N(CH$_2$—O—Z)$_2$ | —O—Z | —O—Z |
| —S— | —N(CH$_2$CH$_2$—O—Z)$_2$ | —N(CH$_2$CH$_2$—O—Z)$_2$ | —N(CH$_2$CH$_2$—O—Z)$_2$ | —N(CH$_2$CH$_2$—O—Z)$_2$ | —O—Z | —O—Z |
| —S— | —N(CH$_2$OH)$_2$ | —N(CH$_2$OH)$_2$ | —N(CH$_2$OH)$_2$ | —N(CH$_2$OH)$_2$ | —OH | —OH |
| —S— | —N(CH$_2$NH$_2$)$_2$ | —N(CH$_2$NH$_2$)$_2$ | —N(CH$_2$NH$_2$)$_2$ | —N(CH$_2$NH$_2$)$_2$ | —OH | —OH |
| —S— | —N(CH$_2$CH$_2$OH)$_2$ | —N(CH$_2$CH$_2$OH)$_2$ | —N(CH$_2$CH$_2$OH)$_2$ | —N(CH$_2$CH$_2$OH)$_2$ | —OH | —OH |
| —S— | —O—Z | —O—Z | —O—Z | —O—Z | —O—Z | —O—Z |
| —S— | —O—C—(CH$_3$)$_3$ | —O—C—(CH$_3$)$_3$ | —O—C—(CH$_3$)$_3$ | —O—C—(CH$_3$)$_3$ | —OH | —OH |
| —S— | —O—(CH$_2$)$_{10}$—CH$_3$. | —O—(CH$_2$)$_{10}$—CH$_3$ | —O—(CH$_2$)$_{10}$—CH$_3$ | —O—(CH$_2$)$_{10}$—CH$_3$ | —OH | —OH |
| —S— | —OH or —O—Z | —OH or —O—Z | —OH or —O—Z | —OH or —O—Z | —OH or —O—Z | —OH or —O—Z |
| —S— | —OH | —OH | —OH | —OH | —OH | —OH |

In some embodiments, compounds of formula II may have the following substitutions at each of, independently, X, $R_1$, $R_2$, $R_3$, $R_4$, $R_5$ and $R_6$, as shown in Table 6:

TABLE 6

| X | $R_1$ | $R_2$ | $R_3$ | $R_4$ | $R_5$ | $R_6$ |
|---|---|---|---|---|---|---|
| —S(=O)$_2$— | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, | —OH, or —O—Z. | —OH, or —O—Z. |

TABLE 6-continued

| X | $R_1$ | $R_2$ | $R_3$ | $R_4$ | $R_5$ | $R_6$ |
|---|---|---|---|---|---|---|
| | —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | | |
| —S(=O)$_2$— | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —OH, or —O—Z. | —OH, or —O—Z. |
| —S(=O)$_2$— | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —OH, or —O—Z. | —OH, or —O—Z. |
| —S(=O)$_2$— | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —OH, or —O—Z. | —OH, or —O—Z. |
| —S(=O)$_2$— | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —OH, or —O—Z. | —OH, or —O—Z. |
| —S(=O)$_2$— | —N(Z)$_2$ | —N(Z)$_2$ | —N(Z)$_2$ | —N(Z)$_2$ | —O—Z | —O—Z |
| —S(=O)$_2$— | —N(CH$_2$—O—Z)$_2$ | —N(CH$_2$—O—Z)$_2$ | —N(CH$_2$—O—Z)$_2$ | —N(CH$_2$—O—Z)$_2$ | —O—Z | —O—Z |
| —S(=O)$_2$— | —N(CH$_2$CH$_2$—O—Z)$_2$ | —N(CH$_2$CH$_2$—O—Z)$_2$ | —N(CH$_2$CH$_2$—O—Z)$_2$ | —N(CH$_2$CH$_2$—O—Z)$_2$ | —O—Z | —O—Z |
| —S(=O)$_2$— | —N(CH$_2$OH)$_2$ | —N(CH$_2$OH)$_2$ | —N(CH$_2$OH)$_2$ | —N(CH$_2$OH)$_2$ | —OH | —OH |
| —S(=O)$_2$— | —N(CH$_2$NH$_2$)$_2$ | —N(CH$_2$NH$_2$)$_2$ | —N(CH$_2$NH$_2$)$_2$ | —N(CH$_2$NH$_2$)$_2$ | —OH | —OH |
| —S(=O)$_2$— | —N(CH$_2$CH$_2$OH)$_2$ | —N(CH$_2$CH$_2$OH)$_2$ | —N(CH$_2$CH$_2$OH)$_2$ | —N(CH$_2$CH$_2$OH)$_2$ | —OH | —OH |
| —S(=O)$_2$— | —O—Z | —O—Z | —O—Z | —O—Z | —O—Z | —O—Z |
| —S(=O)$_2$— | —O—C—(CH$_3$)$_3$ | —O—C—(CH$_3$)$_3$ | —O—C—(CH$_3$)$_3$ | —O—C—(CH$_3$)$_3$ | —OH | —OH |
| —S(=O)$_2$— | —O—(CH$_2$)$_{10}$—CH$_3$ | —O—(CH$_2$)$_{10}$—CH$_3$ | —O—(CH$_2$)$_{10}$—CH$_3$ | —O—(CH$_2$)$_{10}$—CH$_3$ | —OH | —OH |
| —S(=O)$_2$— | —OH or —O—Z | —OH or —O—Z | —OH or —O—Z | —OH or —O—Z | —OH or —O—Z | —OH or —O—Z |
| —S(=O)$_2$— | —OH | —OH | —OH | —OH | —OH | —OH |

In some embodiments, compounds of formula II may have the following substitutions at each of, independently, X, $R_1$, $R_2$, $R_3$, $R_4$, $R_5$ and $R_6$, as shown in Table 7:

TABLE 7

| X | $R_1$ | $R_2$ | $R_3$ | $R_4$ | $R_5$ | $R_6$ |
|---|---|---|---|---|---|---|
| —S(=O)— | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, or —O—Z. | —OH, or —O—Z. |
| —S(=O)— | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —OH, or —O—Z. | —OH, or —O—Z. |

TABLE 7-continued

| X | $R_1$ | $R_2$ | $R_3$ | $R_4$ | $R_5$ | $R_6$ |
|---|---|---|---|---|---|---|
| —S(=O)— | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —OH, or —O—Z. | —OH, or —O—Z. |
| —S(=O)$_2$— | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —OH, or —O—Z. | —OH, or —O—Z. |
| —S(=O)— | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —OH, or —O—Z. | —OH, or —O—Z. |
| —S(=O)— | —N(Z)$_2$ | —N(Z)$_2$ | —N(Z)$_2$ | —N(Z)$_2$ | —O—Z | —O—Z |
| —S(=O)— | —N(CH$_2$—O—Z)$_2$ | —N(CH$_2$—O—Z)$_2$ | —N(CH$_2$—O—Z)$_2$ | —N(CH$_2$—O—Z)$_2$ | —O—Z | —O—Z |
| —S(=O)— | —N(CH$_2$CH$_2$—O—Z)$_2$ | —N(CH$_2$CH$_2$—O—Z)$_2$ | —N(CH$_2$CH$_2$—O—Z)$_2$ | —N(CH$_2$CH$_2$—O—Z)$_2$ | —O—Z | —O—Z |
| —S(=O)— | —N(CH$_2$OH)$_2$ | —N(CH$_2$OH)$_2$ | —N(CH$_2$OH)$_2$ | —N(CH$_2$OH)$_2$ | —OH | —OH |
| —S(=O)— | —N(CH$_2$NH$_2$)$_2$ | —N(CH$_2$NH$_2$)$_2$ | —N(CH$_2$NH$_2$)$_2$ | —N(CH$_2$NH$_2$)$_2$ | —OH | —OH |
| —S(=O)— | —N(CH$_2$CH$_2$OH)$_2$ | —N(CH$_2$CH$_2$OH)$_2$ | —N(CH$_2$CH$_2$OH)$_2$ | —N(CH$_2$CH$_2$OH)$_2$ | —OH | —OH |
| —S(=O)— | —O—Z | —O—Z | —O—Z | —O—Z | —O—Z | —O—Z |
| —S(=O)— | —O—C—(CH$_3$)$_3$ | —O—C—(CH$_3$)$_3$ | —O—C—(CH$_3$)$_3$ | —O—C—(CH$_3$)$_3$ | —OH | —OH |
| —S(=O)— | —O—(CH$_2$)$_{10}$—CH$_3$ | —O—(CH$_2$)$_{10}$—CH$_3$ | —O—(CH$_2$)$_{10}$—CH$_3$ | —O—(CH$_2$)$_{10}$—CH$_3$ | —OH | —OH |
| —S(=O)— | —OH or —O—Z | —OH or —O—Z | —OH or —O—Z | —OH or —O—Z | —OH or —O—Z | —OH or —O—Z |
| —S(=O)— | —OH | —OH | —OH | —OH | —OH | —OH |

In some embodiments, compounds of formula II may have the following substitutions at each of, independently, X, $R_1$, $R_2$, $R_3$, $R_4$, $R_5$ and $R_6$, as shown in Table 8:

TABLE 8

| X | $R_1$ | $R_2$ | $R_3$ | $R_4$ | $R_5$ | $R_6$ |
|---|---|---|---|---|---|---|
| —CH(CCl$_3$)— | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, or —O—Z. | —OH, or —O—Z. |
| —CH(CCl$_3$)— | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —OH, or —O—Z. | —OH, or —O—Z. |
| —CH(CCl$_3$)— | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —OH, or —O—Z. | —OH, or —O—Z. |
| —CH(CCl$_3$)— | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —OH, or —O—Z. | —OH, or —O—Z. |
| —CH(CCl$_3$)— | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —OH, or —O—Z. | —OH, or —O—Z. |
| —CH(CCl$_3$)— | —N(Z)$_2$ | —N(Z)$_2$ | —N(Z)$_2$ | —N(Z)$_2$ | —O—Z | —O—Z |
| —CH(CCl$_3$)— | —N(CH$_2$—O—Z)$_2$ | —N(CH$_2$—O—Z)$_2$ | —N(CH$_2$—O—Z)$_2$ | —N(CH$_2$—O—Z)$_2$ | —O—Z | —O—Z |
| —CH(CCl$_3$)— | —N(CH$_2$CH$_2$—O—Z)$_2$ | —N(CH$_2$CH$_2$—O—Z)$_2$ | —N(CH$_2$CH$_2$—O—Z)$_2$ | —N(CH$_2$CH$_2$—O—Z)$_2$ | —O—Z | —O—Z |
| —CH(CCl$_3$)— | —N(CH$_2$OH)$_2$ | —N(CH$_2$OH)$_2$ | —N(CH$_2$OH)$_2$ | —N(CH$_2$OH)$_2$ | —OH | —OH |

TABLE 8-continued

| X | $R_1$ | $R_2$ | $R_3$ | $R_4$ | $R_5$ | $R_6$ |
|---|---|---|---|---|---|---|
| —CH(CCl$_3$)— | —N(CH$_2$NH$_2$)$_2$ | —N(CH$_2$NH$_2$)$_2$ | —N(CH$_2$NH$_2$)$_2$ | —N(CH$_2$NH$_2$)$_2$ | —OH | —OH |
| —CH(CCl$_3$)— | —N(CH$_2$CH$_2$OH)$_2$ | —N(CH$_2$CH$_2$OH)$_2$ | —N(CH$_2$CH$_2$OH)$_2$ | —N(CH$_2$CH$_2$OH)$_2$ | —OH | —OH |
| —CH(CCl$_3$)— | —O—Z | —O—Z | —O—Z | —O—Z | —O—Z | —O—Z |
| —CH(CCl$_3$)— | —O—C—(CH$_3$)$_3$ | —O—C—(CH$_3$)$_3$ | —O—C—(CH$_3$)$_3$ | —O—C—(CH$_3$)$_3$ | —OH | —OH |
| —CH(CCl$_3$)— | —O—(CH$_2$)$_{10}$—CH$_3$ | —O—(CH$_2$)$_{10}$—CH$_3$ | —O—(CH$_2$)$_{10}$—CH$_3$ | —O—(CH$_2$)$_{10}$—CH$_3$ | —OH | —OH |
| —CH(CCl$_3$)— | —OH or —O—Z | —OH or —O—Z | —OH or —O—Z | —OH or —O—Z | —OH or —O—Z | —OH or —O—Z |
| —CH(CCl$_3$)— | —OH | —OH | —OH | —OH | —OH | —OH |

In some embodiments, compounds of formula II may have the following substitutions at each of, independently, X, $R_1$, $R_2$, $R_3$, $R_4$, $R_5$ and $R_6$, as shown in Table 9:

TABLE 9

| X | $R_1$ | $R_2$ | $R_3$ | $R_4$ | $R_5$ | $R_6$ |
|---|---|---|---|---|---|---|
| —C(Cl)$_2$— | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, or —O—Z. | —OH, or —O—Z. |
| —C(Cl)$_2$— | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —OH, or —O—Z. | —OH, or —O—Z. |
| —C(Cl)$_2$— | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —OH, or —O—Z. | —OH, or —O—Z. |
| —C(Cl)$_2$— | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —OH, or —O—Z. | —OH, or —O—Z. |
| —C(Cl)$_2$— | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —OH, or —O—Z. | —OH, or —O—Z. |
| —C(Cl)$_2$— | —N(Z)$_2$ | —N(Z)$_2$ | —N(Z)$_2$ | —N(Z)$_2$ | —O—Z | —O—Z |
| —C(Cl)$_2$— | —N(CH$_2$—O—Z)$_2$ | —N(CH$_2$—O—Z)$_2$ | —N(CH$_2$—O—Z)$_2$ | —N(CH$_2$—O—Z)$_2$ | —O—Z | —O—Z |
| —C(Cl)$_2$— | —N(CH$_2$CH$_2$—O—Z)$_2$ | —N(CH$_2$CH$_2$—O—Z)$_2$ | —N(CH$_2$CH$_2$—O—Z)$_2$ | —N(CH$_2$CH$_2$—O—Z)$_2$ | —O—Z | —O—Z |
| —C(Cl)$_2$— | —N(CH$_2$OH)$_2$ | —N(CH$_2$OH)$_2$ | —N(CH$_2$OH)$_2$ | —N(CH$_2$OH)$_2$ | —OH | —OH |
| —C(Cl)$_2$— | —N(CH$_2$NH$_2$)$_2$ | —N(CH$_2$NH$_2$)$_2$ | —N(CH$_2$NH$_2$)$_2$ | —N(CH$_2$NH$_2$)$_2$ | —OH | —OH |
| —C(Cl)$_2$— | —N(CH$_2$CH$_2$OH)$_2$ | —N(CH$_2$CH$_2$OH)$_2$ | —N(CH$_2$CH$_2$OH)$_2$ | —N(CH$_2$CH$_2$OH)$_2$ | —OH | —OH |
| —C(Cl)$_2$— | —O—Z | —O—Z | —O—Z | —O—Z | —O—Z | —O—Z |
| —C(Cl)$_2$— | —O—C—(CH$_3$)$_3$ | —O—C—(CH$_3$)$_3$ | —O—C—(CH$_3$)$_3$ | —O—C—(CH$_3$)$_3$ | —OH | —OH |
| —C(Cl)$_2$— | —O—(CH$_2$)$_{10}$—CH$_3$ | —O—(CH$_2$)$_{10}$—CH$_3$ | —O—(CH$_2$)$_{10}$—CH$_3$ | —O—(CH$_2$)$_{10}$—CH$_3$ | —OH | —OH |
| —C(Cl)$_2$— | —OH or —O—Z | —OH or —O—Z | —OH or —O—Z | —OH or —O—Z | —OH or —O—Z | —OH or —O—Z |
| —C(Cl)$_2$— | —OH | —OH | —OH | —OH | —OH | —OH |

In some embodiments, compounds of formula II may have the following substitutions at each of, independently, X, $R_1$, $R_2$, $R_3$, $R_4$, $R_5$ and $R_6$, as shown in Table 10:

TABLE 10

| X | $R_1$ | $R_2$ | $R_3$ | $R_4$ | $R_5$ | $R_6$ |
|---|---|---|---|---|---|---|
| —C(F)$_2$— | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, —O—Z, —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, —N(CH$_2$CH$_2$OH)$_2$, —NH$_2$, —CH$_2$—O—Z, —CH$_2$CH$_2$—O—Z, —CH$_2$OH, —CH$_2$NH$_2$, —CH$_2$—Y, —O—C—(CH$_3$)$_3$, or —O-(alkylene)-CH$_3$. | —OH, or —O—Z. | —OH, or —O—Z. |
| —C(F)$_2$— | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —N(Z)$_2$, —N(CH$_2$—O—Z)$_2$, —N(CH$_2$—CH$_2$—O—Z)$_2$, —N(CH$_2$OH)$_2$, —N(CH$_2$NH$_2$)$_2$, or —N(CH$_2$CH$_2$OH)$_2$. | —OH, or —O—Z. | —OH, or —O—Z. |
| —C(F)$_2$— | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —N(Z)$_2$, —N(CH$_2$—O—Z)$_2$, or —N(CH$_2$—CH$_2$—O—Z)$_2$. | —OH, or —O—Z. | —OH, or —O—Z. |
| —C(F)$_2$— | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —N(CH$_2$OH)$_2$, —N(CH$_2$NH$_2$)$_2$, or —N(CH$_2$CH$_2$OH)$_2$. | —OH, or —O—Z. | —OH, or —O—Z. |
| —C(F)$_2$— | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —O—C—(CH$_3$)$_3$, or —O—(CH$_2$)$_{10}$—CH$_3$ | —OH, or —O—Z. | —OH, or —O—Z. |
| —C(F)$_2$— | —N(Z)$_2$ | —N(Z)$_2$ | —N(Z)$_2$ | —N(Z)$_2$ | —O—Z | —O—Z |
| —C(F)$_2$— | —N(CH$_2$—O—Z)$_2$ | —N(CH$_2$—O—Z)$_2$ | —N(CH$_2$—O—Z)$_2$ | —N(CH$_2$—O—Z)$_2$ | —O—Z | —O—Z |
| —C(F)$_2$— | —N(CH$_2$CH$_2$—O—Z)$_2$ | —N(CH$_2$CH$_2$—O—Z)$_2$ | —N(CH$_2$CH$_2$—O—Z)$_2$ | —N(CH$_2$CH$_2$—O—Z)$_2$ | —O—Z | —O—Z |
| —C(F)$_2$— | —N(CH$_2$OH)$_2$ | —N(CH$_2$OH)$_2$ | —N(CH$_2$OH)$_2$ | —N(CH$_2$OH)$_2$ | —OH | —OH |
| —C(F)$_2$— | —N(CH$_2$NH$_2$)$_2$ | —N(CH$_2$NH$_2$)$_2$ | —N(CH$_2$NH$_2$)$_2$ | —N(CH$_2$NH$_2$)$_2$ | —OH | —OH |
| —C(F)$_2$— | —N(CH$_2$CH$_2$OH)$_2$ | —N(CH$_2$CH$_2$OH)$_2$ | —N(CH$_2$CH$_2$OH)$_2$ | —N(CH$_2$CH$_2$OH)$_2$ | —OH | —OH |
| —C(F)$_2$— | —O—Z | —O—Z | —O—Z | —O—Z | —O—Z | —O—Z |
| —C(F)$_2$— | —O—C—(CH$_3$)$_3$ | —O—C—(CH$_3$)$_3$ | —O—C—(CH$_3$)$_3$ | —O—C—(CH$_3$)$_3$ | —OH | —OH |
| —C(F)$_2$— | —O—(CH$_2$)$_{10}$—CH$_3$ | —O—(CH$_2$)$_{10}$—CH$_3$ | —O—(CH$_2$)$_{10}$—CH$_3$ | —O—(CH$_2$)$_{10}$—CH$_3$ | —OH | —OH |
| —C(F)$_2$— | —OH or —O—Z | —OH or —O—Z | —OH or —O—Z | —OH or —O—Z | —OH or —O—Z | —OH or —O—Z |
| —C(F)$_2$— | —OH | —OH | —OH | —OH | —OH | —OH |

Exemplary compounds represented by formula II include, but are not limited to:

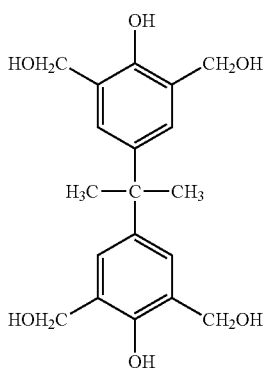

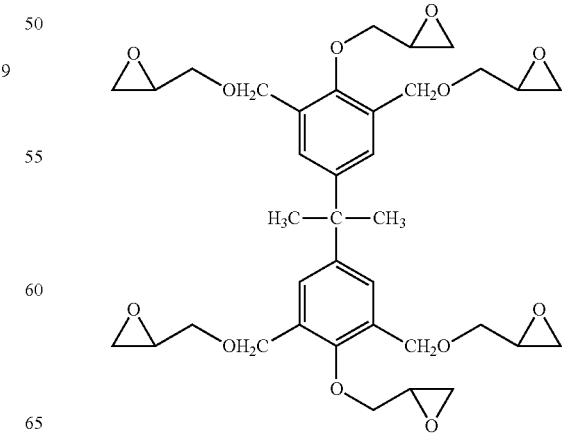

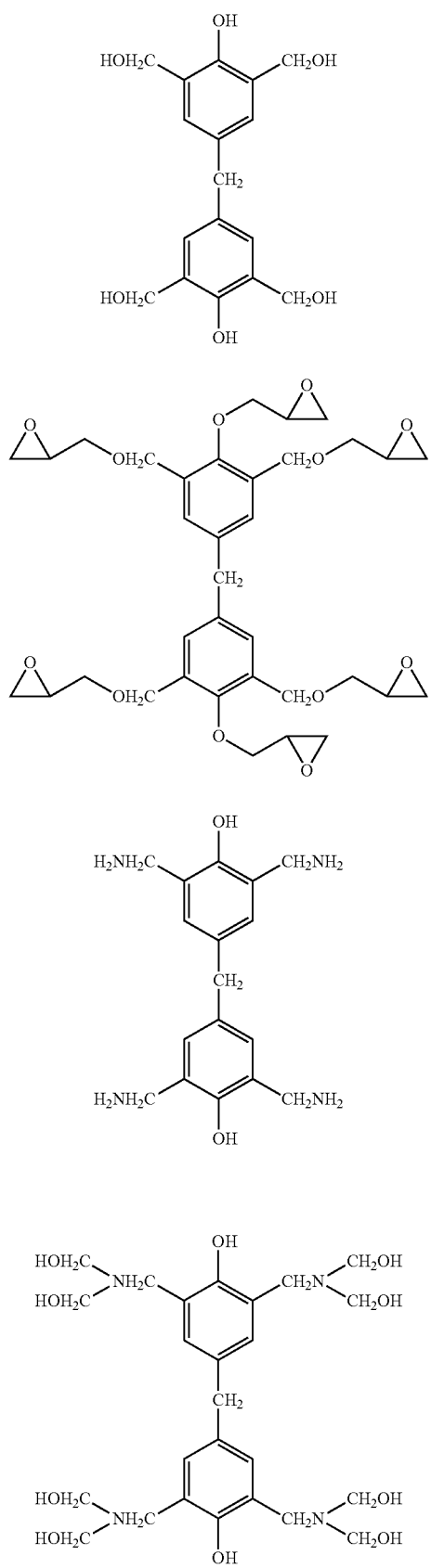
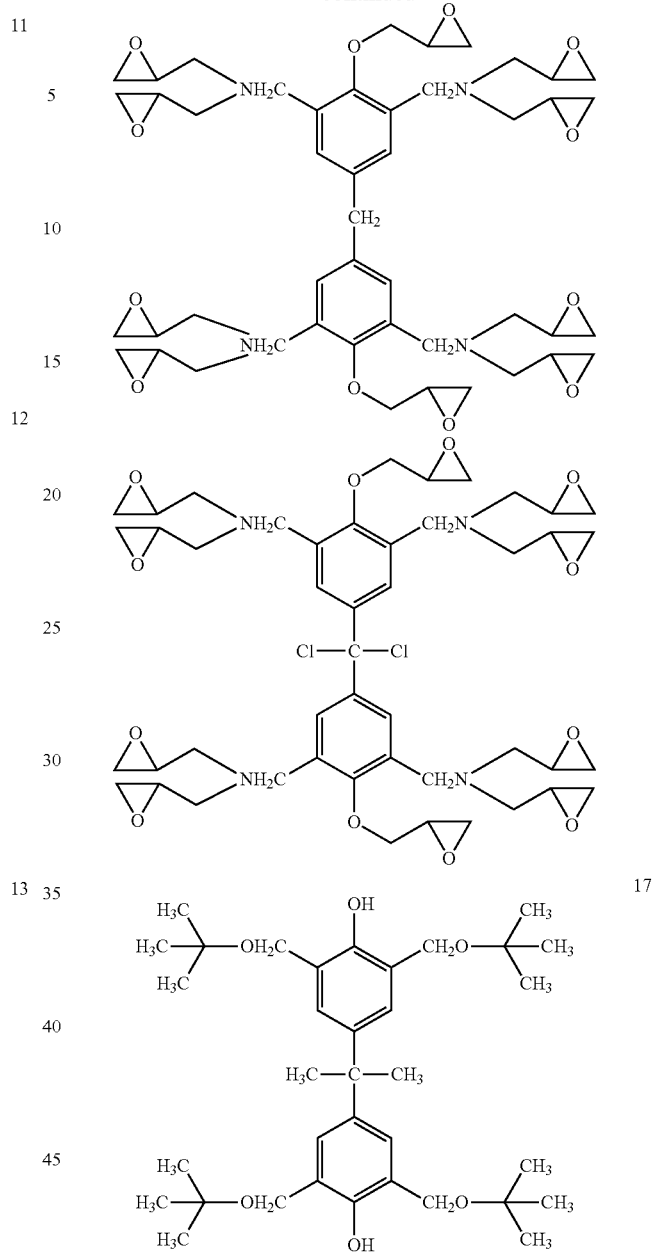

In some embodiments, a method for preparing compounds described herein may include: (a) contacting a phenolic compound with a formaldehyde or paraformaldehyde to form a hydroxymethyl compound; and (b) contacting the hydroxymethyl compound with an epihalohydrin compound, a diethanolamine compound, or an ammonia to form the compound described herein.

In some embodiments, contacting the phenolic compound with the formaldehyde or paraformaldehyde is performed in the presence of a basic catalyst. Specific examples of the basic catalyst include alkali metal hydroxides, such as KOH, LiOH, NaOH, and the like. Non-limiting examples of phenolic compounds that may be used are phenol, bisphenol A, bisphenol F, bisphenol S, bisphenol sulphone, bisphenol sulfoxide, bisphenol chloral, bisphenolvinylidene dichloride, and bisphenol methylenedifluoride. The phenolic compound and the formaldehyde or paraformaldehyde may be reacted in a molar ratio from about 1:3 to about 1:5, about 1:3 about 1:4.5, or about 1:3 to about 1:4. Specific examples include about 1:5, about 1:4, about 1:3.5, about 1:3 and ranges between any two of these values (including their endpoints). During the reaction of the phenolic compound and the formaldehyde or paraformaldehyde, the pH of the solution may be maintained between about pH 8 to about pH 10, about pH 8 to about pH 9.5, about pH 8 to about pH 9, or about pH 8 to about pH 8.5. Specific examples include about pH 8, about pH 8.5, about pH 9, about pH 9.5, about pH 10, and ranges between any two of these values (including their endpoints).

During the reaction of the phenolic compound and the formaldehyde or paraformaldehyde, the phenolic compound and the formaldehyde may be heated to a temperature of about 50° C. to about 70° C., about 50° C. to about 65° C., or about 50° C. to about 60° C. Specific examples also include about 50° C., about 55° C., about 60° C., about 65° C., about 70° C., and ranges between (and including the endpoints of) any two of these values. The heating may be performed for about 2 hours to about 6 hours, for about 2 hours to about 5 hours, for about 2 hours to about 4 hours, or for about 2 hours to about 3 hours. Specific examples include about 2 hours, about 3 hours, about 4 hours, about 5 hours, about 6 hours, and ranges between (an including the endpoints of) any two of these values. The reaction time may vary with the reaction temperature inversely. For example, higher the reaction temperature, shorter is the reaction time period.

The reaction between the phenolic compound and the formaldehyde may result in the formation of hydroxymethyl compounds such as trihydroxymethyl phenol, tetrahydroxymethyl bisphenol A, tetrahydroxymethyl bisphenol F, tetrahydroxymethyl bisphenol S, tetrahydroxymethyl bisphenol sulphone, tetrahydroxymethyl bisphenol sulfoxide, tetrahydroxymethyl bisphenol chloral, tetrahydroxymethyl bisphenolvinylidene dichloride, and tetrahydroxymethyl bisphenol methylenedifluoride.

In some embodiments, contacting the hydroxymethyl compound with the epihalohydrin compound may include reacting the hydroxymethyl compound with the epihalohydrin compound in a molar ratio from about 1:2 to about 1:10, about 1:2 to about 1:7, about 1:2 to about 1:6, or about 1:2 to about 1:4. Specific examples include about 1:2, about 1:4, about 1:6, about 1:8, about 1:10, and ranges between any two of these values. The molar ratio of epihalohydrin to the hydroxymethyl compound may also depend on the number of the hydroxyl groups present on the hydroxymethyl compound, and taking into consideration that one epihalohydrin molecule may react with one hydroxyl group. In some embodiments, the epihalohydrin molecule may be used in molar excess of the hydroxyl groups. Examples of the epihalohydrin compound that may be used in the reaction include, but are not limited to, epichlorohydrin, epibromohydrin and methylepichlorohydrin. In some embodiments, the hydroxymethyl compound and the epihalohydrin compound may be heated to a temperature of about 50° C. to about 90° C., about 50° C. to about 75° C., about 50° C. to about 70° C., or about 50° C. to about 60° C. Specific examples also include about 50° C., about 65° C., about 70° C., about 80° C., about 85° C., about 90° C., and ranges between (and including the endpoints of) any two of these values. The heating may be performed for about 2 hours to about 6 hours, for about 2 hours to about 5 hours, for about 2 hours to about 4 hours, or for about 2 hours to about 3 hours. Specific examples include about 2 hours, about 3 hours, about 4 hours, about 5 hours, about 6 hours, and ranges between (and including the endpoints of) any two of these values. In some embodiments, the reaction may involve a two-step heating process, wherein the first step may involve heating the reaction mixture to a lower temperature followed by a second step of heating the reaction mixture at a higher temperature to obtain a high degree of condensation of epihalohydrin and hydroxymethyl compound.

The reactions between the hydroxymethyl compound and the epihalohydrin compound may be performed in the presence of a reaction catalyst. Suitable reaction catalysts include, but are not limited to, $MgClO_4$, LiCl, LiOH, $SnF_2$, $LiClO_4$, or a combination thereof. In addition, the reaction rate may be increased by adding an organic solvent and carrying the reaction in an emulsion system. Examples of the organic solvent include, but are not limited to, 1-butanol, secondary butanols, glycol ethers such as 2-methoxyethanol, 2-ethoxyethanol, and 2-phenoxyethanol, ethers such as 1,4-dioxane, 1,3-dioxane and diethoxyethane, and aprotic polar solvents such as acetonitrile, dimethyl sulfoxide, and dimethyl formamide. These organic solvents may be used alone or in combination so as to adjust polarity.

For the purpose of, for example, improving the reaction rate, the reaction may be conducted in the presence of a phase transfer catalyst, such as, for example, quaternary ammonium salts. Examples include benzyltrimethylammonium bromide, cetyltrimethylammonium bromide, tetrabutylammonium hydroxide, tetrabutyl ammonium chloride and any combination thereof.

The reaction product obtained from the above methods described herein may be washed with, for example, water. Using the resulting product of the reaction between the hydroxymethyl compound and the epihalohydrin compound as an example, the unreacted epihalohydrin compound and the organic solvent may be distilled off by distillation with heating under reduced pressure. To obtain a compound containing a small amount of a hydrolysable halogen, the dehydrochlorination step may be performed under optimum conditions so that all the chlorohydrin derivatives are converted to epoxides. To remove the salt content, the resulting product may be dissolved in an organic solvent, such as toluene, methyl isobutyl ketone or methyl ethyl ketone, and the salt can be removed by filtration or by washing with water. The organic solvent may be distilled off by heating under reduced pressure to obtain a high-purity epoxy resin.

In some embodiments, contacting the hydroxymethyl compound with the diethanolamine may include reacting the hydroxymethyl compound with the diethanolamine in a in a molar ratio from about 1:2 to about 1:10, about 1:2 to about 1:7, about 1:2 to about 1:6, or about 1:2 to about 1:5. Specific examples include about 1:2, about 1:4, about 1:6, about 1:8, about 1:10, and ranges between any two of these values. The molar ratio of diethanolamine to the hydroxymethyl compound may also depend on the number of the hydroxyl groups present on the hydroxymethyl compound, and taking into consideration that one diethanolamine molecule may react with one hydroxyl group. In some embodiments, the diethanolamine molecule may be used in molar excess of the hydroxyl groups. In some embodiments, the hydroxymethyl compound and the diethanolamine may be heated to a temperature of about 50° C. to about 70° C., about 50° C. to about 65° C., about 50° C. to about 60° C., or about 50° C. to about 55° C. Specific examples also include about 50° C., about 55° C., about 60° C., about 70° C., and ranges between (and including the endpoints of) any two of these values. The heating may be performed for about 2 hours to about 6 hours, for about 2 hours to about 5 hours, for about 2 hours to about 4 hours, or for about 2 hours to about 3 hours. Specific examples include about 2 hours, about 3 hours, about 4 hours, about 5 hours, about 6 hours, and ranges between (an including the endpoints of) any two of these values.

The reactions between the hydroxymethyl compound and the diethanolamine compound may be performed in the presence of a reaction catalyst. Suitable reaction catalysts include, but are not limited to, $MgClO_4$, $LiCl$, $LiOH$, $SnF_2$, $LiClO_4$, or a combination thereof. In addition, the reaction rate may be increased by adding an organic solvent and carrying the reaction in an emulsion system. Examples of the organic solvent include, but are not limited to, acetone, methyl ethyl ketone, methanol, tetrahydrofuran, 1,4-dioxane, 1,3-dioxane, diethoxyethane, dimethyl sulfoxide, dimethyl formamide, and combinations thereof.

In some embodiments, contacting the hydroxymethyl compound with an ammonia may involve contacting the hydroxymethyl compound and ammonia in a molar ratio from about 1:1 to about 1:1.5, about 1:1 about 1:1.3, about 1:1 to about 1:1.2, or about 1:1 to about 1:1.1. Specific examples include about 1:1, about 1:1.1, about 1:1.2, about 1:1.3, about 1:1.5, and ranges between any two of these values. The hydroxymethyl compound and the ammonia may be heated to a temperature of about 50° C. to about 70° C., about 50° C. to about 65° C., about 50° C. to about 60° C., or about 50° C. to about 55° C. Specific examples also include about 50° C., about 55° C., about 65° C., about 70° C., and ranges between (and including the endpoints of) any two of these values. In some embodiments, the hydroxymethyl compound and the ammonia may be heated under a pressure of about 1 atmosphere to about 1.5 atmospheres, about 1 atmosphere to about 1.35 atmospheres, or about 1 atmosphere to about 1.15 atmospheres. Specific examples include about 1 atmosphere, about 1.15 atmospheres, about 1.25 atmospheres, about 1.35 atmospheres, about 1.5 atmospheres, and ranges between (and including the endpoints of) any two of these values.

Compounds of the present disclosure may be used as, for example, hardeners, activators or cross-linking agents in various resins. These compounds may enhance the thermal stability, glass transition temperature and/or the chemical resistance of the resins due to the aromatic structures and multi-functionality. Exemplary resins in which the compounds may be incorporated include, but are not limited to, polyurethanes, silicones, commercial epoxy resins, urea-formaldehyde resins, melamine-formaldehyde resins, hydroxymethyl urea-formaldehyde resins, hydroxymethyl melamine-formaldehyde resins and the like.

In addition, compounds of the present disclosure may be cured to form resins. A variety of curing agents may be used for this process. Curing agents include, but are not limited to, aliphatic, cycloaliphatic, polycycloaliphatic or aromatic diamines; aliphatic, cycloaliphatic, polycycloaliphatic or aromatic polyamines; dicarboxylic acids and anhydrides thereof; aromatic hydroxyl containing compounds; imidazoles; and guanidines. Suitable curing agents also include, but are not limited to, methylenedianiline, 4,4'-diaminostilbene, 4,4'-diamino-α-methylstilbene, 4,4'-diaminobenzanilide, dicyandiamide, ethylenediamine, diethylene triamine, triethylene tetraamine, sulfanilamide, diamino diphenylsulfone, t-butyltoluenediamine, bis-4-aminocyclohexylamine, hexamethylenediamine, piperazine, aminoethylpiperazine, 2,5-dimethyl-2,5-hexanediamine, 1,12-dodecanediamine, tris-3-aminopropylamine and combinations thereof.

Resins manufactured from the compounds of the present disclosure may be blended with, for example, other materials such as solvents or diluents, fillers, pigments, dyes, flow modifiers, thickeners, reinforcing agents, mold release agents, wetting agents, stabilizers, fire retardant agents, surfactants and combinations thereof. These additives may be added in functionally equivalent amounts to obtain the desired properties.

Solvents which may be employed include, but are not limited to, hydrocarbons, glycol ethers, aliphatic ethers, cyclic ethers, esters, amides and combinations thereof. Suitable solvents or diluents include toluene, xylene, methyl ethyl ketone, methyl isobutyl ketone, diethylene glycol methyl ether, dipropylene glycol methyl ether, dimethylformamide, N-methylpyrrolidinone, tetrahydrofuran, 1,4-dioxane, propylene glycol methyl ether and any combination thereof.

Diluents that may be use are styrene oxide, alkylphenyl monoglycidyl ether, alkyl monoglycidyl ether, cyclohexene oxide, and the like.

Reinforcing materials which may be employed include, but are not limited to, natural and synthetic fibers in the form of woven fabric, mats, monofilament, multifilament, unidirectional fibers, ravings, random fibers or filaments, inorganic fillers or whiskers, hollow spheres, and the like. Suitable reinforcing materials include, but are not limited to, glass, ceramics, nylon, rayon, cotton, aramid, graphite, polyalkylene terephthalates, polyethylene, polypropylene, polyesters and any combination thereof.

Suitable fillers which may be employed herein include, but are not limited to, inorganic oxides, ceramic microspheres, plastic microspheres, glass microspheres, inorganic whiskers, calcium carbonate and any combination thereof.

The poly-functional epoxy and amine resins prepared according to the disclosure may have a high glass transition temperature and may display high thermal stability. Resins with such properties may be well suited for use as, for example, binders for composite materials. Further, the multi-functional epoxy resins may have a higher degree of cross-linking resulting in improved resistance to solvents and/or corrosive chemicals. The resins made from the compounds of the present disclosure may have improved water miscibility when compared to the common aromatic epoxy resins, and accordingly such resins may be used for applications in, for example, a humid environment, wet surfaces, water based epoxies for construction work and water based paints.

The resins of the present disclosure may be employed in, for example, encapsulations, electronic or structural laminates or composites, filament winding, molding, semiconductor encapsulating materials, under-fill materials, conductive pastes, laminates, resin compositions used for electronic circuit boards, resin casting materials, adhesives, interlayer insulation materials for buildup substrates, and coating materials, such as insulating paint. Further, these resins may also be used as linings in articles of manufacture including, but not limited to, tanks, cars, drums, pails, pipes, down-hole oilfield tubings, and food cans. In addition, the resins may be used as, for example, laminated epoxy structures for concrete molds, honeycomb cores, wood and metal assemblies, and reinforced pipes.

Epoxy resins of the present disclosure may be used with, for example, acrylic systems to provide excellent coatings for articles of manufacture such as, appliances, kitchen cabinets, outdoor furniture, aluminum siding, and other metal products. The poly-functional epoxy and amine resins may be used as, for example, a powder coating for anti-corrosion or as high sheen decorative coating. Such coatings may find applications in articles of manufacture such as, washing machines, appliances, ships and bridges, pipelines, chemical plants, automobiles, farm implements, containers, and floor surfaces.

EXAMPLES

Example 1

Preparation of Tetraglycidylether Resol (Compound 6)

About 100 grams of phenol and 270 grams of formalin solution (37% concentration) were mixed in a five-neck reaction flask fitted with a condenser, mechanical stirrer, dropping funnel, and a thermometer. The reaction was started by adding 100 ml of 40% sodium hydroxide solution dropwise, and the pH of the reaction mixture was adjusted to 10. The reaction mixture was heated to about 65° C. for 2 hours, and the pH was maintained between 9 and 10. At the end of this period, the reaction mixture was cooled and neutralized with cold (5-10° C.) solution of sodium dihydrogen phosphate. The oily viscous layer was separated, dissolved in ethanol, desalted, and dried with molecular sieves. The product was evaporated by rotary evaporators and dried under vacuum to obtain the resol compound.

About 45.5 grams (0.25 mole) of the above obtained resol was combined with 1 gram of $MgClO_4$ dissolved in 5 mL of 2-methoxy ethanol, and 231 grams (2.5 mole) of epichlorohydrin. The system was flashed with nitrogen for 10 minutes with continuous mixing. The reaction temperature was raised to 60° C., and the reaction was continued for two hours. At the end of this period, the temperature was further raised to 80-85° C., and the reaction was continued for 1 more hour. Later, the reaction mixture was cooled to 60° C., and about 12 grams of tetrabutyl ammonium chloride dissolved in 25 mL water was added with continuous mixing, followed by addition of 250 ml of 50% NaOH solution. The reaction mixture was stirred for 1 hour, and the mixture of epichlorohydrin and water was separated by azeotropic distillation. Separated epichlorohydrin was again introduced back into the reaction mixture, and the mixture was further heated to 70° C. for 60 minutes. The excess of unreacted epichlorohydrin was distilled under vacuum, and the reaction mixture was cooled to room temperature. The epoxy product formed was dissolved in toluene, filtered, washed with 1% acetic acid, and dried with molecular sieves. The product was evaporated by rotary evaporators and dried under vacuum at 0.1 millimeter Hg at 40° C. for 6 hours to obtain a brownish colored viscous compound 6. The epoxy equivalent of the compound was determined by adopting standard methods. The epoxy equivalent was found to be 86 grams/equivalent (epoxy equivalent=5.5 eq/kg), viscosity at 40° C. was 115.4 Pa s, and active chlorine content was 1.3%.

Example 2

Preparation of Triamino Resol (Compound 1)

About 100 grams of phenol and 270 grams of formalin solution (37% concentration) were mixed in a five-neck reaction flask fitted with a condenser, mechanical stirrer, dropping funnel, and a thermometer. The reaction was started by adding 100 ml of 40% sodium hydroxide solution dropwise, and the pH of the reaction mixture was adjusted to 10. The reaction mixture was heated to about 65° C. for 2 hours, and the pH was maintained between 9 and 10. At the end of this period, the reaction mixture was cooled and neutralized with cold (5-10° C.) solution of sodium dihydrogen phosphate. The oily viscous layer was separated, dissolved in ethanol, desalted, and dried with molecular sieves. The product was evaporated by rotary evaporators and dried under vacuum to obtain the resol compound.

About 30.6 grams of the above resol was mixed with 150 mL of methanol in a one liter auto-clave system from Analis-Belgium that is fitted with mechanical stirrer, and which could be operated under controlled temperature and pressure. The system was secured and connected to ammonia gas cylinder. The system was flushed with $N_2$, and mixed for 10 minutes to dissolve the resol Ammonia gas was feed to the autoclave until the pressure reached 1.5 atmospheres. The reaction temperature was maintained at 50-70° C. via the cooling jacket of the autoclave for 2 hours. At the end of this period, the system was cooled to room temperature and the system was flushed with $N_2$ gas to remove unreacted ammonia gas. The white milky syrup product was evaporated and dried under vacuum to obtain compound 1.

Example 3

Preparation of Compound 2

About 30 grams of Compound 1 and 270 grams of formalin solution (37% concentration) were mixed in a five-neck reaction flask fitted with a condenser, mechanical stirrer, dropping funnel, and a thermometer. The reaction was started by adding 40% sodium hydroxide solution dropwise, and the pH of the reaction mixture was adjusted to 10. The reaction mixture was heated to about 65° C. for 2 hours, and the pH was maintained between 9 and 10. At the end of this period, the reaction mixture was cooled and neutralized with cold (5-10° C.) solution of sodium dihydrogen phosphate. The oily viscous layer was separated, dissolved in ethanol, desalted, and dried with molecular sieves. The product was evaporated by rotary evaporators and dried under vacuum to obtain compound 2. The number of hydroxyl groups was evaluated by DSC and spectrophotometry using ceric ammonium nitrate.

Example 4

Preparation of N-Glycidyl Amino Resol (Compound 3)

About 105.5 grams (0.5 mole) of compound 1 dissolved in 100 mL of DMF was combined with 1 gram of $MgClO_4$ dissolved in 5 mL of 2-methoxy ethanol and 350 grams of epichlorohydrin in a 1 Liter reaction vessel fitted with an efficient mechanical stirrer, condenser, thermometer, dropping funnel, and a gas inlet tube. The system was flashed with nitrogen for 10 minutes with continuous mixing. The reaction temperature was raised to 60° C., and the reaction was continued for two hours. At the end of this period, the temperature was further raised to 80-85° C., and the reaction was continued for 1 more hour. Later, the reaction mixture was cooled to 60° C., and about 12 grams of tetrabutyl ammonium chloride dissolved in 25 mL water was added with constant mixing, followed by addition of 250 ml of 50% NaOH solution. The reaction mixture was stirred for 1 hour, and the mixture of epichlorohydrin and water was distilled by azeotropic distillation. Epichlorohydrin was separated and again introduced back into the reaction mixture, and the mixture was further heated to 70° C. for 60 minutes. The excess of unreacted epichlorohydrin was distilled under vacuum and the reaction mixture was cooled to room temperature. The epoxy product formed was dissolved in toluene, filtered, washed with 1% acetic acid, and dried with molecular sieves. The product was evaporated by rotary evaporators and dried under vacuum at 0.1 millimeter Hg at 40° C. for 6 hours to obtain compound 3. The epoxy equivalent was found to be 4.93 eq/kg, viscosity at 40° C. was 215.4 Pa s, and active chlorine content was 0.34%.

Example 5

Preparation of Compound 5

About 30.6 grams of Compound 2 was mixed with 500 mL of methanol in a one liter auto-clave system from Analis-Belgium that is fitted with mechanical stirrer, and which could be operated under controlled temperature and pressure. The system was secured and connected to ammonia gas cylinder. The system was flushed with $N_2$, and mixed for 10 minutes to dissolve the compound Ammonia gas was feed to the autoclave until the pressure reached 1.5 atmospheres. The reaction temperature was maintained at 50-60° C. via the cooling jacket of the autoclave for 2 hours. At the end of this period, the system was cooled to room temperature and the system was flushed with $N_2$ gas to remove unreacted ammonia gas. The product was evaporated and dried under vacuum to obtain a waxy compound 5. The compound was evaluated as a crosslinking agent for epoxy resins.

Example 6

Preparation of Compound 7

About 22.25 grams of compound 2 is combined with 1 gram of $MgClO_4$ dissolved in 5 mL of 2-methoxy ethanol, and 231 grams (2.5 mole) of epichlorohydrin. The system is flashed with nitrogen for 10 minutes with continuous mixing. The reaction temperature is raised to 60° C., and the reaction is continued for two hours. At the end of this period, the temperature is further raised to 80-85° C., and the reaction is continued for 1 more hour. Later, the reaction mixture is cooled to 60° C., and about 12 grams of tetrabutyl ammonium chloride dissolved in 25 mL water is added with constant mixing, followed by addition of 250 ml of 50% NaOH solution. The reaction mixture is stirred for 1 hour, and the mixture of epichlorohydrin and water is distilled by azeotropic distillation. Epichlorohydrin is separated and again introduced back into the reaction mixture, and the mixture is further heated to 70° C. for 60 minutes. The excess of unreacted epichlorohydrin is distilled under vacuum, and the reaction mixture is cooled to room temperature. The epoxy product formed is dissolved in toluene, filtered, washed with 1% acetic acid, and dried with molecular sieves. The product is evaporated by rotary evaporators and dried under vacuum at 0.1 millimeter Hg at 40° C. for 6 hours to obtain compound 7.

Example 7

Preparation of Compound 4

About 60 grams (0.6 mole) of diethanolamine was obtained in a three-neck reaction vessel fitted with condenser, magnetic stirrer, and a dropping funnel. About 33.6 grams of resol compound of Example 1 diluted with 10 mL of ethanol was added dropwise for one hour at 60° C. and the reaction mixture was heated to 70° C. The reaction was continued with efficient mixing for further one hour. At the end of the reaction, about 200 grams of cold water was added to dissolve the unreacted diethanolamine. The product obtained was re-dissolved in ethanol, dried with molecular sieves (4 A), evaporated by rotary evaporator, and dried under vacuum at 60° C. and 0.1 millimeter Hg for 6 hours to obtain a brownish viscous compound 4. The product was evaluated as a crosslinking agent for polyurethanes.

Example 8

Preparation of Compound 8

About 22.25 grams of compound 4 was combined with 1 gram of $MgClO_4$ dissolved in 5 mL of 2-methoxy ethanol, and 231 grams (2.5 mole) of epichlorohydrin. The system was flashed with nitrogen for 10 minutes with continuous mixing. The reaction temperature was raised to 80° C., and the reaction was continued for two hours. At the end of this period, the temperature was further raised to 90° C., and the reaction was continued for 1 more hour. Later, the reaction mixture was cooled to 60° C., and about 12 grams of tetrabutyl ammonium chloride dissolved in 25 mL water was added with constant mixing, followed by addition of 250 ml of 50% NaOH solution. The reaction mixture was stirred for 1 hour, and the mixture of epichlorohydrin and water was distilled by azeotropic distillation. Epichlorohydrin was separated and again introduced back into the reaction mixture, and the mixture was further heated to 70° C. for 60 minutes. The excess of unreacted epichlorohydrin was distilled under vacuum, and the reaction mixture was cooled to room temperature. The epoxy product formed was dissolved in toluene, filtered, washed with 1% acetic acid, and dried with molecular sieves. The product was evaporated by rotary evaporators and dried under vacuum at 0.1 millimeter Hg at 40° C. for 6 hours to obtain compound 8. The epoxy equivalent was found to be 5.95 eq/kg, viscosity at 40° C. was 185.4 Pa s, and active chlorine content was 0.56%.

Example 9

Preparation of Hydroxymethyl Bisphenols
(Compounds 9 and 11)

About 50 grams of bisphenol A and 270 grams of formalin solution (37% concentration) were mixed in a five-neck reaction flask fitted with a condenser, mechanical stirrer, dropping funnel, and a thermometer. The reaction was started by adding 40% sodium hydroxide solution dropwise, and the pH of the reaction mixture was adjusted to between 9 and 10. The reaction mixture was heated to about 65° C. for 2 hours, and the pH was maintained between 9 and 10. At the end of this period, the reaction mixture was cooled and neutralized with cold (5-10° C.) solution of sodium dihydrogen phosphate. The oily viscous layer was separated, dissolved in ethanol, desalted, and dried with molecular sieves. The product was evaporated by rotary evaporators and dried under vacuum to obtain compound 9.

Similarly, compound 11 could be obtained by similar methods using bisphenol F as the starting material.

Example 10

Preparation of Hexaglycidylether Bisphenols
(Compounds 10 and 12)

About 22.25 grams of compound 9 was combined with 1 gram of $MgClO_4$ dissolved in 5 mL of 2-methoxy ethanol, and 231 grams (2.5 mole) of epichlorohydrin in a 1 Liter reaction vessel fitted with an efficient mechanical stirrer, condenser, thermometer, dropping funnel, and a gas inlet tube. The system was flashed with nitrogen for 10 minutes with continuous mixing. The reaction temperature was raised to 60° C., and the reaction was continued for two hours. At the end of this period, the temperature was further raised to 80-85° C., and the reaction was continued for 1 more hour. Later, the reaction mixture was cooled to 60° C. and about 12 grams of tetrabutyl ammonium chloride dissolved in 25 mL water was added with constant mixing, followed by the addition of 250 ml of 50% NaOH solution. The reaction mixture was stirred for 1 hour, and the mixture of epichlorohydrin and water was distilled by azeotropic distillation. Epichlorohydrin was separated and again introduced back into the reaction mixture and the mixture was further heated to 70° C. for 60 minutes. The excess of unreacted epichlorohydrin was distilled under vacuum and the reaction mixture was cooled to room temperature. The epoxy product formed was dissolved in toluene, filtered, washed with 1% acetic acid, and dried with molecular sieves. The product was evaporated by rotary evaporators and dried under vacuum at 0.1 millimeter Hg at 40° C. for 6 hours to obtain compound 10. The epoxy equivalent was found to be 5.1 eq/kg, viscosity at 40° C. was 225.4 Pa s, and active chlorine content was 1.15%.

Similarly, compound 12 could be prepared by reacting epichlorohydrin with compound 11 as shown above.

Example 11

Preparation of Tetrabutyloxymethylene Bisphenol (Compound 17)

About 45.5 grams of compound 9 dissolved in 30% tetrahydrofuran was combined with 2.5 moles of t-butyl alcohol, and 1 gram of zeolite Na/Al catalyst in a 1 Liter reaction vessel fitted with an efficient mechanical stirrer, condenser, thermometer, dropping funnel, and a gas inlet tube. The reaction mixture was heated gradually to 60° C. for 2 hours. The reaction was terminated by heating the reaction mixture on a hot plate. The product was neutralized with 1% acetic acid to obtain a viscous compound 17. The product was used as an antioxidant and as a plasticizer.

Example 12

Curing of an Epoxy Compound 10 grams of compound 6 prepared in Example 1 was mixed with 3 grams of the commercial hardener 8050 (supplied by Parchem). The mixture was left to cure overnight to form a hard resin with a glass transition temperature of about 90° C. to about 100° C.

Example 13

Curing of an Epoxy Compound 30 grams of lignin based epoxy resin is mixed with 10 grams of compound 6 prepared in Example 1 and 10 grams commercial hardener type 8050 (equivalent weight 85.9). The mixture is left to cure overnight to form a tough resin composite.

Example 14

An Article Coated with Epoxy Coating

A cast iron rod is coated with an epoxy paint prepared from compound 3. A similar rod is also coated with a commercially available non-epoxy paint. The paint is allowed to dry and scribed with an X through the paint down to the metal. The rods are placed in a salt fog chamber (5% NaCl, 35° C.) for 200 hours. At the end of this period, the rods are visually inspected for corrosion and peeling of the paint at the site of damage. The rod sprayed with epoxy paint will display less corrosion and peeling of the paint, when compared to the rod sprayed with a non-epoxy paint.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," and so on). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, and so on" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, and so on). In those instances where a convention analogous to "at least one of A, B, or C, and so on" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, and so on). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, and so on. As a non-limiting example, each range discussed herein can be readily broken down into a lower third, middle third and upper third, and so on. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A compound of Formula I:

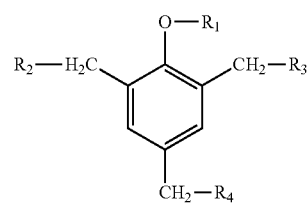

wherein:

$R_1$ is H or Z;

$R_2$ is —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —O—Z, —CH$_2$—O—Z, —CH$_2$CH$_2$—O—Z, —CH$_2$OH, or —O—C—(CH$_3$)$_3$;

$R_3$ is —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —O—Z, —CH$_2$—O—Z, —CH$_2$CH$_2$—O—Z, —CH$_2$OH or —O—C—(CH$_3$)$_3$;

$R_4$ is —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, —O—Z, —CH$_2$—O—Z, —CH$_2$CH$_2$—O—Z, —CH$_2$OH or —O—C—(CH$_3$)$_3$; and Z is

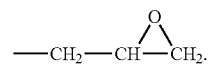

2. The compound of claim 1, wherein:

$R_1$ is H or Z;

$R_2$ is —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, or;

$R_3$ is —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, or; and $R_4$ is —N(Z)$_2$, —N(CH$_2$—O—Z)$_2$, —N(CH$_2$CH$_2$—O—Z)$_2$, —N(CH$_2$OH)$_2$, —N(CH$_2$NH$_2$)$_2$, or.

3. The compound of claim 1, wherein:

$R_1$ is Z;

$R_2$ is —N(Z)$_2$, —N(CH$_2$—O—Z)$_2$, or —N(CH$_2$CH$_2$—O—Z)$_2$;

$R_3$ is —N(Z)$_2$, —N(CH$_2$—O—Z)$_2$, or —N(CH$_2$CH$_2$—O—Z)$_2$; and $R_4$ is —N(Z)$_2$, —N(CH$_2$—O—Z)$_2$, or —N(CH$_2$CH$_2$—O—Z)$_2$.

4. The compound of claim 1, wherein $R_1$ is Z, $R_2$ is —N(Z)$_2$, $R_3$ is —N(Z)$_2$, and $R_4$ is —N(Z)$_2$.

5. The compound of claim 1, wherein $R_1$ is Z, and each of $R_2$ is —N(CH$_2$—O—Z)$_2$, $R_3$ is —N(CH$_2$—O—Z)$_2$, and $R_4$ is —N(CH$_2$—O—Z)$_2$.

6. The compound of claim 1, wherein $R_1$ is Z, and each of $R_2$ is —N(CH$_2$CH$_2$—O—Z)$_2$, $R_3$ is —N(CH$_2$CH$_2$—O—Z)$_2$, and $R_4$ is —N(CH$_2$CH$_2$—O—Z)$_2$.

7. The compound of claim 1, wherein:

$R_1$ is H;

$R_2$ is —N(CH$_2$OH)$_2$ or —N(CH$_2$NH$_2$);

$R_3$ is —N(CH$_2$OH)$_2$ or —N(CH$_2$NH$_2$); and $R_4$ is —N(CH$_2$OH)$_2$ or —N(CH$_2$NH$_2$).

8. The compound of claim 1, wherein $R_1$ is H, $R_2$ is —N(CH$_2$OH)$_2$, $R_3$ is —N(CH$_2$OH)$_2$, and $R_4$ is —N(CH$_2$OH)$_2$.

9. The compound of claim 1, wherein $R_1$ is H, $R_2$ is —N(CH$_2$NH$_2$)$_2$, $R_3$ is —N(CH$_2$NH$_2$)$_2$, and $R_4$ is —N(CH$_2$NH$_2$)$_2$.

10. The compound of claim 1, wherein $R_1$ is H, $R_2$ is —N(CH$_2$—O—Z)$_2$, $R_3$ is —N(CH$_2$—O—Z)$_2$, and $R_4$ is —N(CH$_2$—O—Z)$_2$.

* * * * *

UNITED STATES PATENT AND TRADEMARK OFFICE
CERTIFICATE OF CORRECTION

PATENT NO. : 9,890,130 B2  
APPLICATION NO. : 14/768218  
DATED : February 13, 2018  
INVENTOR(S) : Adam Page 1 of 1

It is certified that error appears in the above-identified patent and that said Letters Patent is hereby corrected as shown below:

In the Specification

In Column 30, Line 13, delete "resol Ammonia" and insert -- resol. Ammonia --, therefor.

In Column 31, Line 20, delete "compound Ammonia" and insert -- compound. Ammonia --, therefor.

In Column 35, Line 14, delete "recitation no" and insert -- recitation, no --, therefor.

In Column 35, Line 35, delete "general such" and insert -- general, such --, therefor.

In Column 35, Line 43, delete "general such" and insert -- general, such --, therefor.

In the Claims

In Column 36, Line 63, in Claim 2, delete "—N(CH$_2$NH$_2$)$_2$, or;" and insert -- or —N(CH$_2$NH$_2$)$_2$; --, therefor.

In Column 36, Line 65, in Claim 2, delete "—N(CH$_2$NH$_2$)$_2$, or; and" and insert -- or —N(CH$_2$NH$_2$)$_2$; and --, therefor.

In Column 36, Line 67, in Claim 2, delete "—N(CH$_2$NH$_2$)$_2$, or." and insert -- or —N(CH$_2$NH$_2$)$_2$. --, therefor.

Signed and Sealed this  
Third Day of July, 2018

Andrei Iancu  
*Director of the United States Patent and Trademark Office*